(12) United States Patent
Cook et al.

(10) Patent No.: US 8,173,809 B2
(45) Date of Patent: May 8, 2012

(54) CYSTEINE AND CYSTINE PRODRUGS TO TREAT SCHIZOPHRENIA AND REDUCE DRUG CRAVINGS

(75) Inventors: James M. Cook, Milwaukee, WI (US); David A. Baker, Grafton, WI (US); Wenyuan Yin, Milwaukee, WI (US); Edward Merle Johnson, II, Glendale, WI (US)

(73) Assignees: Marquette University, Milwaukee, WI (US); UWM Research Foundation, Inc., Milwaukee, WI (US)

( * ) Notice: Subject to any disclaimer, the term of this patent is extended or adjusted under 35 U.S.C. 154(b) by 158 days.

(21) Appl. No.: 12/367,867

(22) Filed: Feb. 9, 2009

(65) Prior Publication Data
US 2009/0281109 A1    Nov. 12, 2009

Related U.S. Application Data

(60) Provisional application No. 61/026,874, filed on Feb. 7, 2008.

(51) Int. Cl.
*C07D 295/00* (2006.01)
(52) U.S. Cl. .................................. 544/385; 544/349
(58) Field of Classification Search .............. 544/349, 544/385
See application file for complete search history.

(56) References Cited

U.S. PATENT DOCUMENTS

| | | | |
|---|---|---|---|
| 5,589,473 | A | 12/1996 | Geiwiz et al. |
| 2005/0032708 | A1 | 2/2005 | Bush et al. |
| 2006/0270647 | A1 | 11/2006 | Coric et al. |

FOREIGN PATENT DOCUMENTS

| | | | |
|---|---|---|---|
| DE | 4228455 A1 | 9/1994 | |
| EP | 0463514 A1 | 1/1992 | |
| EP | 0499882 A1 | 8/1992 | |
| EP | 0999204 A1 | 5/2000 | |
| EP | 1004302 A2 | 5/2000 | |
| EP | 1120407 A1 | 8/2001 | |
| EP | 1195259 A2 | 4/2002 | |
| EP | 1364943 A1 | 11/2003 | |
| EP | 1374831 A1 | 1/2004 | |
| FR | 2159183 A | 6/1973 | |
| WO | 91/18594 A1 | 12/1991 | |
| WO | 97/46229 A1 | 12/1997 | |
| WO | 01/37788 A1 | 5/2001 | |
| WO | 0211676 A2 | 2/2002 | |
| WO | 03/045359 A2 | 6/2003 | |
| WO | 2004/030522 A2 | 4/2004 | |
| WO | 2004/108692 A1 | 12/2004 | |
| WO | 2008008380 A1 | 1/2008 | |

OTHER PUBLICATIONS

Shumpei Sakaibara, Hisaya Tani: "Synthesis of Polycysteine," Bull. Chem. Soc., Japan, vol. 29, 1956, pp. 85-88.

Erwin Brand, Marta Sandberg: "The lability of the sulfur in cystine derivatives and its possible bearing on the constitution of insulin," J. Biol. Chem., vol. 70, 1926, pp. 381-395.

Database Crossfire Beilstein Beilstein Institute Zur Foerderung Der Wissenschaften, Franfurt Am Main, DE; Database accession No. 5753808 & Marc J. O. Anteunis, Chr. Becu, A. Kolodziejcz;yk, Bogdan Liberek: Bull. Soc. Chim. Belges, vol. 90, No. 8, 1981, pp. 785-802.

Database Crossfire Beilstein Beilstein Institute Zur Foerderung Der Wissenschaften, Franfurt Am Main, DE; Database accession No. 5753809 & A. Kolodziejczyk, Bogdan Liberek: Bull. Soc. Chim. Beiges, vol. 90, No. 8, 1981, pp. 785-802.

Database Crossfire Beilstein Beilstein Institute Zur Foerderung Der Wissenschaften, Franfurt Am Main, DE; Database accession No. 844285 & Blaha et al.: Collection of Czechoslovak Chemical Communications, vol. 31, 1966, pp. 4296-4298.

Database Crossfire Beilstein Beilstein Institute Zur Foerderung Der Wissenschaften, Franfurt Am Main, DE; Database accession No. 3978029 & Blaha et al.: Collection of Czechoslovak Chemical Communications, vol. 31, 1966, pp. 4296-4298.

Database Crossfire Beilstein Beilstein Institute Zur Foerderung Der Wissenschaften, Franfurt Am Main, DE; Database accession No. 3986193 & Blaha et al.: Collection of Czechoslovak Chemical Communications, vol. 31, 1966, pp. 4296-4298.

Database Crossfire Beilstein Beilstein Institute Zur Foerderung Der Wissenschaften, Franfurt Am Main, DE; Database accession No. 72669 & Jesse P. Greenstein: "Studies of multivalent amino acids and peptides" J. Biol. Chem., vol. 118, No. 2, 1937, pp. 321-329.

Database Crossfire Beilstein Beilstein Institute Zur Foerderung Der Wissenschaften, Franfurt Am Main, DE; Database accession No. 800081 & A. P. Hope, B. Halpern: Australian Journal of Chemistry, vol. 29, 1976, pp. 1591-1603.

Database Crossfire Beilstein Beilstein Institute Zur Foerderung Der Wissenschaften, Franfurt Am Main, DE; Database accession No. 665766 & Wenck, Schneider: Experientia, vol. 27, 1971, pp. 20-22.

Database Crossfire Beilstein Beilstein Institute Zur Foerderung Der Wissenschaften, Franfurt Am Main, DE; Database accession No. 60079 & Abderhalden, Rossner: Hoppe-Seyler's Zeitschrift Fur Physiologische Chemie, vol. 163, 1927, p. 183.

G. Zanotti, F. Pinnen, G. Lucente: Tetrahedron Letters, vol. 26, No. 44, 1984, pp. 5481-5484.

Karl-Hans Ongania: "Selektive Eliminations-Additionsreaktionen" Arch. Pharm., vol. 312, 1979, pp. 963-968.

(Continued)

*Primary Examiner* — James O Wilson
*Assistant Examiner* — Douglas M Willis
(74) *Attorney, Agent, or Firm* — Quarles & Brady LLP

(57) ABSTRACT

The present invention provides cysteine and cystine prodrugs for the treatment of schizophrenia and drug addiction. The invention further encompasses pharmaceutical compositions containing prodrugs and methods of using the prodrugs and compositions for treatment of schizophrenia and drug addiction. Exemplary prodrugs include the cysteine compound having the formula

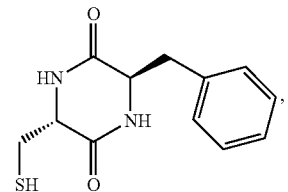

as well as cystine dimers thereof.

7 Claims, 7 Drawing Sheets

OTHER PUBLICATIONS

Database Crossfire Beilstein Beilstein Institute Zur Foerderung Der Wissenschaften, Franfurt Am Main, DE; Database accession No. 50666 & Hooper et al.: J. Chem Soc., vol. 1956, 1956, pp. 3148-3151. Hans Heymann, T. Ginsberg, Z. R. Gulick, E. A. Konopka, R. L. Mayer: "The preparation and some biological properties of the asparagine analog L-2-amino-2-carbocyethanesul fonamide" J. Am. Chem. Soc. vol. 81, 1959, pp. 5125-5128.

Database Crossfire Beilstein Beilstein Institute Zur Foerderung Der Wissenschaften, Franfurt Am Main, DE; Database accession No. 2635366 & Michael Ruf et al.: Chemische Berichte, vol. 129, No. 10, 1996, pp. 1251-1258.

Database Crossfire Beilstein Beilstein Institute Zur Foerderung Der Wissenschaften, Franfurt Am Main, DE; Database accession No. 6702116 & L. Serves, I. Photaki: J. Am. Chem. Soc., vol. 84, 1962, pp. 3887-3897.

Database Crossfire Beilstein Beilstein Institute Zur Foerderung Der Wissenschaften, Franfurt Am Main, DE; Database accession No. 2635070 & Fry: J. Org. Chem., vol. 15, 1950, pp. 438-441.

Database Crossfire Beilstein Beilstein Institute Zur Foerderung Der Wissenschaften, Franfurt Am Main, DE; Database accession No. 3187303 & Foeldi: Acto Chimica Academiae Scientarum Hungaricae, vol. 5, 1955, pp. 187-194.

Database Crossfire Beilstein Beilstein Institute Zur Foerderung Der Wissenschaften, Franfurt Am Main, DE; Database accession No. 2611160 & L. Serves, I. Photaki: J. Am. Chem. Soc. , vol. 84, 1962, pp. 3887-3897.

Database Crossfire Beilstein Beilstein Institute Zur Foerderung Der Wissenschaften, Franfurt Am Main, DE; Database accession No. 1730085 & Pirie: Biochemical Journal, vol. 25, 1931, p. 619.

Database Crossfire Beilstein Beilstein Institute Zur Foerderung Der Wissenschaften, Franfurt Am Main, DE; Database accession No. 10718042 & Eiji Kawanishi, Kyoichi Higuchi, Akihiko Ishida: Heterocycles, vol. 52, No. 1, 2000, pp. 425-443.

Database Crossfire Beilstein Beilstein Institute Zur Foerderung Der Wissenschaften, Franfurt Am Main, DE; Database accession No. 10724708 & Eiji Kawanishi, Kyoichi Higuchi, Akihiko Ishida: Heterocycles, vol. 52, No. 1, 2000, pp. 425-443.

Database Crossfire Beilstein Beilstein Institute Zur Foerderung Der Wissenschaften, Franfurt Am Main, DE; Database accession No. 5323681 & A. I. Meyers, Richard A. Amos: J. Am. Chem. Soc., vol. 102, No. 2, 1980, pp. 870-872.

Database Crossfire Beilstein Beilstein Institute Zur Foerderung Der Wissenschaften, Franfurt Am Main, DE; Database accession No. 2200873 & T. Inui: Bull. Soc. Chem. Japan, vol. 44, No. 9, 1971, pp. 2515-2520.

Baker et al. Neuroadaptations in cystine-glutamate exchange underlie cocaine relapse. Nat Neurosci 2003; 6: 743-749.

Baker et al. Contribution of cystine-glutamate antiporters to the psychotomimetic effects of phencyclindine. Neuropsychopharmacology 2008; 33: 1760-1772.

Berk M. Oxidative stress in bipolar disorder: a double blind randomized placebo controlled trial of N-actyl cysteine as glutathione precursor. Bipolar Disorders 2007; 9(suppl 1): 21.

Larowe et al. Safety and tolerability of N-acetylcysteine in cocaine-dependent individuals. Am J Addict 2006; 15: 105-110.

Madayag et al. Repeated N-acetylcysteine administration alters plasticity-dependent effects of cocaine. J Neurosci 2007; 27: 13968-13976.

Mardikian et al. An open-label trial of N-acetylcysteine for the treatment of cocaine depedence: a pilot study. Prog Neuropsychopharmacol Biol Psychiatry 2007; 31: 389-394.

Moran et al. Cystine/glutamate exchange regulates metabotropic glutamate receptor presynaptic inhibition of excitatory transmission and vulnerability to cocaine seeking. J Neurosci 2005; 25: 6389-6393.

Peters et al. The group II metabotropic glutamate receptor agonist, LY379268, inhibits both cocaine- and food-seeking behavior in rats. Psychopharmacology 2006; 186: 143-149.

Zhao et al. The enantiospecific, stereospecific total synthesis of the ring-A oxygenated sarpagine indole alkaloids (+)-Majvininve, (+)-10-Methoxyaffinisine, and (+)-Na-Methylsarpagine, as well as the total synthesis of the alstonia bisindole alkaloid macralstonidine. J. Org. Chem. 2003; 68: 6279-6295.

Sheehan et al. A new synthesis of cysteinyl peptides. J. Am. Chem. Soc. 1958; 80:1158-1164.

Bressan et al. Synthesis and metal-coordination properties of dimeric cyclo-L-hemicystinyl-glycine. Int. J. Peptide Protein Res. 1986; 28:103-106.

Bernstein et al. Preparation of a diketopiperazine analog of leukotriene D4 (LTD4). Tetrahedron Lett. 1985; 26:1951-1954.

Bull et al. Practical synthesis of schollkopf's bis-lactim ether chiral auxiliary: (3S)-3,6-dihydro-2,5-dimethoxy-3-isopropyl-pyrazine. Tetrahedron:Asymmetry 1998; 9:321-327.

Berk et al. N-acetyl cysteine as a glutathione precursor for schizophrenia—a double-blind, randomized, placebo-controlled trial. Biol. Psychiatry 2008; 64:468-475.

Abderhalden et al. Weitere Beiträge über Dioxo-piperazine sowie über ein aus Leucyl-glycinanhydrid gewonnenes, ungesättiges Anhydrid. Synthese des tertiären Leucins. Z Physiol Chem 1927; 163:149-184.

Rossbach et al. Synthese and Eigenschaften unsymmetrischer Diketopiperazine des Cysteins. Z Naturforsch B 1971; 26:1144-1151.

Bergmann et al. Umlagerungen peptidähnlicher Stoffe. 7. Unwandlung eines cystinhaltigen Diketopiperazines. Z Physiol Chem 1926; 152:189-201.

Schneider et al. Kinetics of the reaction of imidazolesulfhydryl compounds with N-ethylmaleimide. Hoppe-Seyler's Z. Physiol. Chem. , 1969; 350:1521-1530.

Gockel et al. Zinc complexation of cyclic dipeptides containing cysteine and/or histidine. Inorg. Chim. Acta., 2001; 323:16-22.

Greenstein et al. Multivalent amino acids and peptides. VIII. Synthesis of bisanhydro-I-cystinyl-l-cystine and other diketopiperazines of cystine. J. Biol. Chem. , 1937; 118:321-329.

Schneider F. Kooperative Imidazol-SH-Katalyse als enzymatische Modellreaktion. Hoppe-Seyler's Z. Physiol. Chem. , 1967; 348:1034-1042.

Fischer et al. A diketopiperazine derivative with antibacterial activity. Rev. Asoc. Med. Argent. , 1955, 69:21-22.

Angehrn, P. et al., "New Antibacterial Agents Derived from the DNA Gyrase Inhibitor Cyclothialidine," Journal of Medicinal Chemistry, American Chemical Society, Washington, US, vol. 47, No. 6, Jan. 1, 2004, pp. 1487-1513.

Braga, A. L. et al., "'One-Pot' Synthesis of Chiral N-Protected alpha-Amino Acid-Derived 1,2,4-Oxadiazoles," Synthesis, May 26, 2004, pp. 1589-1594.

Grzonka, Z. et al., "Chiroptical Properties of Tetrazole Analogs of Amino Acids," Polish Journal of Chemistry, vol. 52, 1978, pp. 1411-1413.

Brook, et al. "Tetrazole analogues of amino acids and peptides: II. Paper and thin-layer chromatography of tetrazole analogues of amino acids," Journal of Chomatography, vol. 15, No. 2, 1970, pp. 310-313.

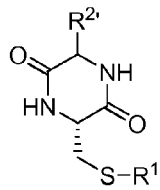

$R^1$ = H
  = tBu
  = SPh
  = C(Ph)$_3$
$R^2$ = Amino acid side chains
  (see Figure 1)

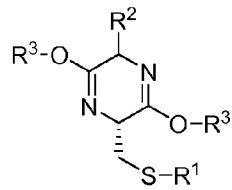

$R^2$ = Amino acid side chains
  (see Figure 1)
$R^3$ = CH$_3$
  = CH$_2$CH$_3$
  = CH(CH$_3$)$_2$

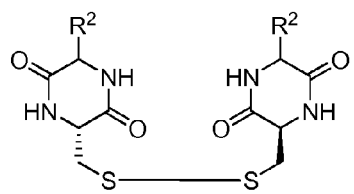

$R^2$ = Amino acid side chains
  (see Figure 1)

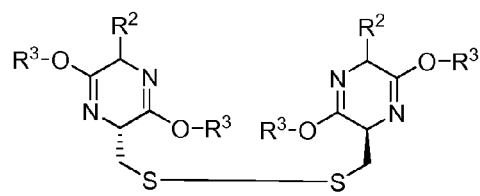

$R^2$ = Amino acid side chains
  (see Figure 1)
$R^3$ = CH$_3$
  = CH$_2$CH$_3$
  = CH(CH$_3$)$_2$

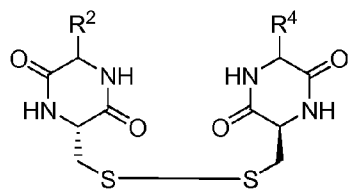

$R^2$ = Amino acid side chains
  (see Figure 1)
$R^4$ = Amino acid side chain
  different from that of $R^2$

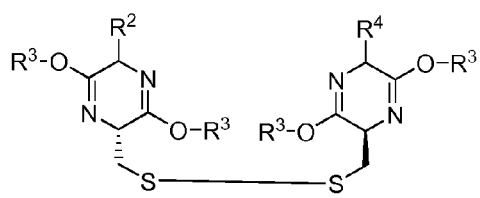

$R^2$ = Amino acid side chains
  (see Figure 1)
$R^3$ = CH$_3$
  = CH$_2$CH$_3$
  = CH(CH$_3$)$_2$
$R^4$ = Amino acid side chain
  different from that of $R^2$

Fig. 2

CYSTEINE AND CYSTINE PRODRUGS TO TREAT SCHIZOPHRENIA AND REDUCE DRUG CRAVINGS

CROSS-REFERENCE TO RELATED APPLICATIONS

The present application claims the benefit of U.S. Provisional application 61/026,874, filed Feb. 7, 2008, which is incorporated herein by reference in its entirety for all purposes.

FIELD OF THE INVENTION

This invention relates generally to the treatment of schizophrenia and drug addiction. More particularly, the present invention is directed to cysteine and cystine prodrugs useful as antipsychotic medications in the treatment of schizophrenia. As well, the respective prodrugs are applicable for reducing drug cravings in drug addicted individuals.

BACKGROUND OF THE INVENTION

Schizophrenia is a debilitating disorder afflicting 1% of the world's population. The development of effective medications to treat schizophrenia is reliant on advances in characterizing the underlying pathophysiology. Chlorpromazine and other phenothiazines are considered first generation antipsychotics (termed "typical antipsychotics") useful in the treatment of schizophrenia. However, the antipsychotic efficacy of phenothiazines was, in fact, serendipitously discovered. These drugs were initially used for their antihistaminergic properties and later for their potential anesthetic effects during surgery. Hamon and colleagues extended the use of phenothiazines to psychiatric patients and quickly uncovered the antipsychotic properties of these compounds; shortly thereafter, the pharmacologic characteristic of dopamine receptor blockade was linked to the antipsychotic action of chlorpromazine (Thorazine). This led to the development of additional dopamine receptor antagonists, including haloperidol (Haldol). For nearly fifty years, dopamine antagonists were the standard treatment for schizophrenia even though these drugs induce severe side effects ranging from Parkinson's disease-like motor impairments to sexual dysfunction and are only effective in treating the positive symptoms of schizophrenia.

In the 1970's, clozapine became the first "atypical psychotic" or 2nd generation antipsychotic agent introduced. Clinical trials have shown that clozapine produces fewer motor side effects and exhibits improved efficacy against positive and negative symptoms relative to 1st generation compounds. However, clozapine was briefly withdrawn from the market because of the potential to produce severe agranulocytosis, a potentially fatal side effect requiring patients to undergo routine, costly hematological monitoring. As a result, clozapine is only approved for treatment-resistant schizophrenia. Although also a dopamine receptor antagonist, the therapeutic site of action for clozapine is thought to involve blockade of serotonin receptors. This led to the generation of other serotonin receptor antagonists in the 1990's with the goal of improving the safety profile of clozapine.

The growth potential for novel antipsychotics was revealed following the introduction of risperidone in 1994; within two years risperidone overtook haloperidol in the number of prescriptions written by physicians. While it was generally assumed that the newer 2nd generation antipsychotics also exhibited the favorable efficacy profile produced by clozapine, the clinical data was ambiguous. As a result, the NIH recently funded a large, lengthy, and expensive clinical trial to examine this assumption. The results of the Clinical Antipsychotic Trials of Intervention Effectiveness (CATIE), recently released, indicate that there is no benefit to the newer 2nd generation compounds. Specifically, 1st and 2nd generation drugs did not differ in the incidence of severe motor side-effects nor were 2nd generation agents found to be more effective than 1st generation antipsychotics. In the CATIE trial, 74% of the patients discontinued treatment prior to completing the 18 month trial, in part due to a lack of efficacy and intolerability of the treatment regimen.

As can be appreciated from the foregoing, there exists a pressing need and considerable market potential for novel antipsychotic agents. Of course, the development of effective antipsychotic agents will be facilitated by a thorough understanding of pathophysiologies underlying the neurological disorders.

SUMMARY OF THE INVENTION

The present invention is based on the inventors' success in identifying prodrugs of cysteine and cystine with utility as antipsychotic and addiction reducing agents. Accordingly, the invention provides a cysteine prodrug having the structure:

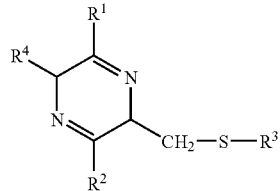

wherein: $R^1$ and $R^2$ are independently selected from OH, =O, or a branched or straight chain $C_1$ to $C_5$ alkoxyl group, with the caveat that when =O is selected the nitrogen atom adjacent the carbonyl group thusly formed bears a H and a single bond joins the adjacent nitrogen to said carbonyl group; $R^3$ is H, a branched or straight chain $C_1$ to $C_5$ alkyl, a nitrobenzenesulfonyl, a trityl, an aryl thio, an aryl, an alkylthio, an acyl, a benzoyl, a thio acyl, a thio benzoyl, or a benzyl group; and $R^4$ is selected from the side chain groups of the natural L-amino acids cys, gly, phe, pro, val, ser, arg, asp, asn, glu, gln, ala, his, ile, leu, lys, met, thr, trp, tyr, or D-isomers thereof, with the caveat that when $R^4$ is the side chain group of the natural L-amino acid gly, $R^1$ and $R^2$ are not both selected to be =O; or a cystine dimer of said prodrug having the structure:

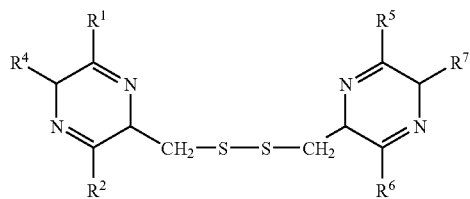

wherein: $R^1$, $R^2$, $R^5$ and $R^6$ are independently selected from OH, =O, or a branched or straight chain $C_1$ to $C_5$ alkoxyl group, with the caveat that when =O is selected the nitrogen atom adjacent the carbonyl group thusly formed bears a H and a single bond joins the adjacent nitrogen to said carbonyl group; and R⁴ and R⁷ are independently selected from the side chain groups of the natural L-amino acids cys, gly, phe, pro, val, ser, arg, asp, asn, glu, gln, ala, his, ile, leu, lys, met, thr, trp, tyr, or D-isomers thereof, with the caveat that when R⁴ and R⁷ are both the side chain group of the natural L-amino acid gly, R¹, R², R⁵ and R⁶ shall not all be selected to be =O.

In certain preferred embodiments, the cysteine prodrug according to the invention has the structure:

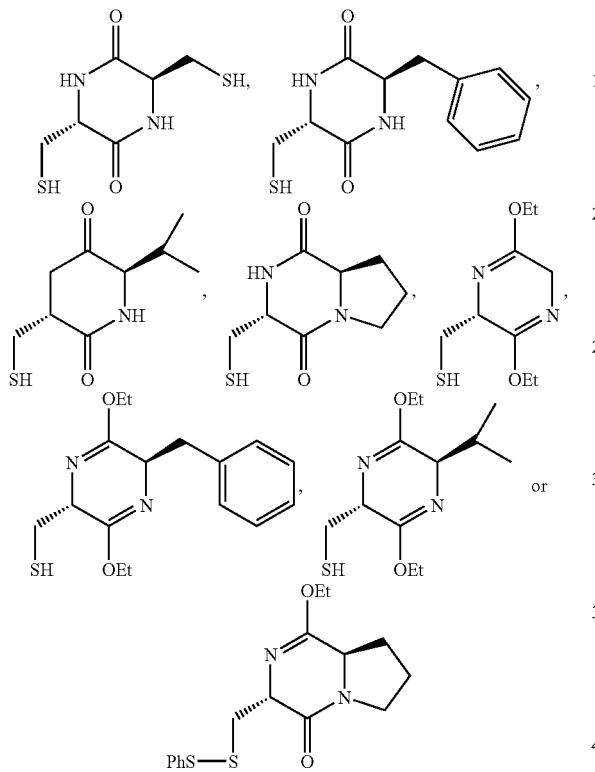

The cysteine prodrug may alternatively be provided in the form of a cystine dimer. Certain preferred cystine dimers according to the invention have the structure: the form of the cystine dimer having the structure:

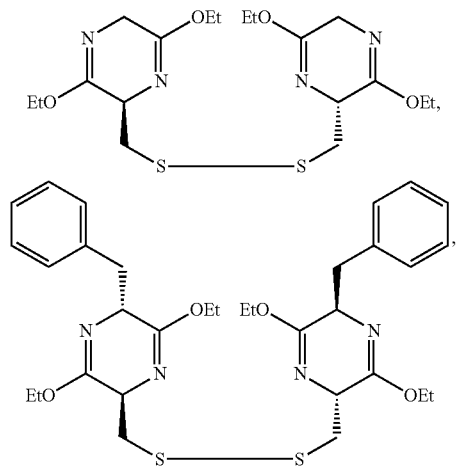

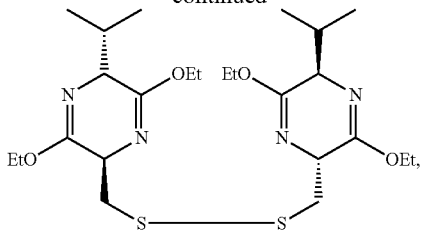

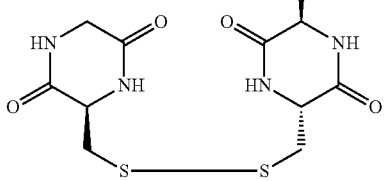

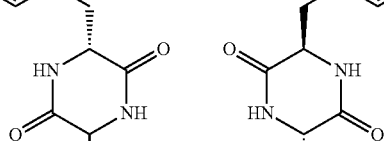

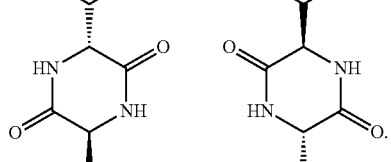

The invention provides synthetic routes for the synthesis of cystine dimers having identical R⁴ and R⁷ groups or, alternatively, mixed or non-identical R⁴ and R⁷ groups.

In certain cysteine prodrugs or cystine dimers of the invention, at least one R⁴ and R⁷ group is a cys and the reactive moiety is further protected by a branched or straight chain $C_1$ to $C_5$ alkyl, a nitrobenzenesulfonyl, a trityl, an aryl thio, an aryl, an alkylthio, an acyl, a benzoyl, a thio acyl, a thio benzoyl, or a benzyl group.

In another aspect, the present invention provides a method of reducing schizophrenia in a subject. Such a method includes steps of administering to the subject an effective amount of a cysteine prodrug or cystine dimer thereof according to the invention, whereby schizophrenia is reduced in the subject. Administration is preferably accomplished by oral delivery.

In yet another aspect, the invention provides a method of reducing drug craving in a subject. Such a method includes steps of administering to the subject an effective amount of a cysteine prodrug or cystine dimer of the invention, whereby drug craving is reduced in the subject. Again, administration is preferably via the oral route.

Of course, the present invention encompasses pharmaceutical compositions including a cysteine prodrug or cystine dimer according to the invention in combination with at least a pharmaceutically-acceptable carrier. The invention further contemplates methods for the manufacture of such a pharmaceutical composition for the reduction of schizophrenia and/or drug craving in a subject.

A further aspect of the invention encompasses protected cysteine analogs having the structure:

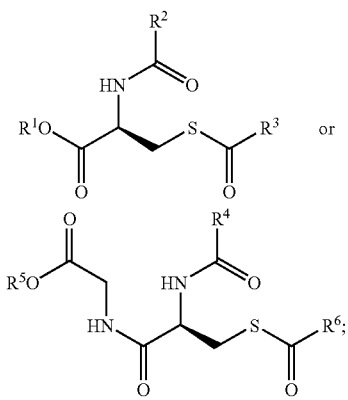

or a cystine dimer of the protected cysteine analog having the structure:

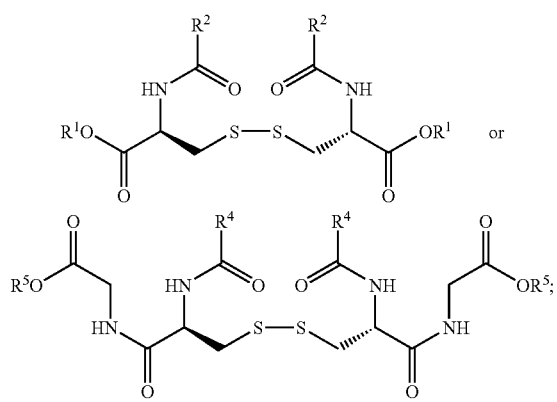

wherein $R^1$ through $R^6$ are independently selected from a branched or straight chain $C_1$ to $C_5$ alkyl, a phenyl, or a benzyl group.

Preferable protected cysteine analogs according to the invention have the structure:

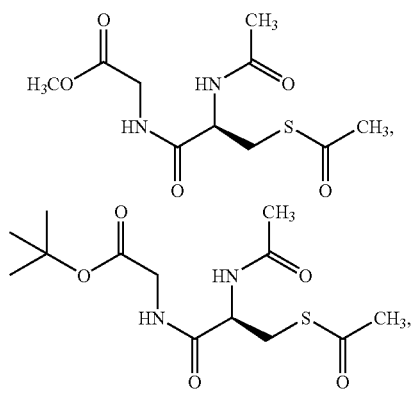

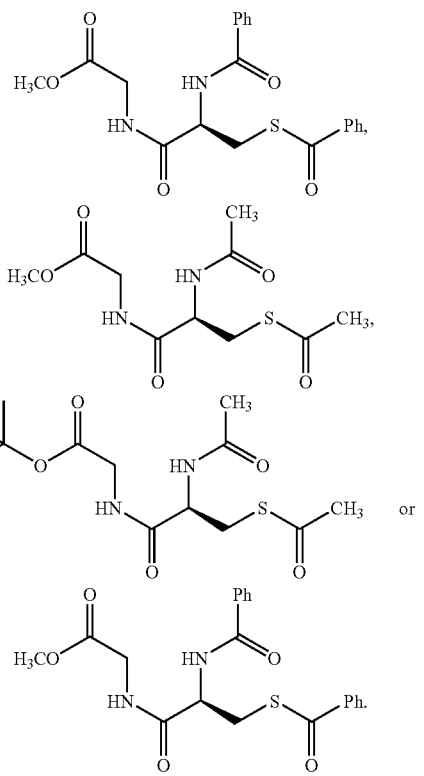

Alternatively, protected cysteine analogs may be provided in the form of the corresponding cystine dimers. Certain preferred cystine dimers have the structures:

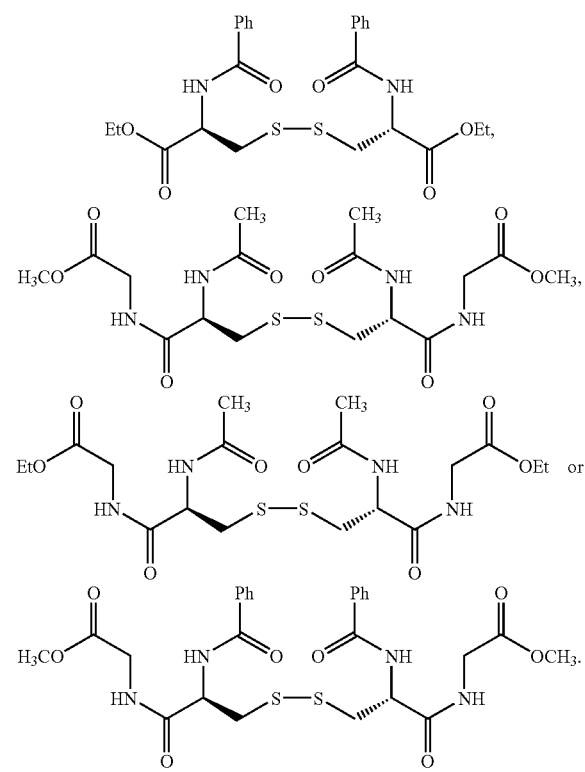

Related to the protected cysteine analogs, the invention further provides a method of reducing schizophrenia in a subject by administering to a subject an effective amount of a protected cysteine analog or cystine dimer thereof according to the invention, whereby schizophrenia is reduced in said subject. Administration is preferably via the oral route.

The invention is also directed to protected cysteine analogs or cystine dimers thereof having any one of the structures described and claimed herein. Such analogs are useful in methods of reducing schizophrenia or reducing drug cravings in a subject comprising administering to the subject an effective amount of the protected cysteine analog or cystine dimer.

The invention further encompasses pharmaceutical compositions containing a protected analog or dimer thereof in combination with a pharmaceutically-acceptable carrier. Methods of formulating/manufacturing such pharmaceutical compositions for the treatment of schizophrenia or for reducing drug craving in a subject are also within the invention's scope.

Other objects, features and advantages of the present invention will become apparent after review of the specification, claims and drawings.

BRIEF DESCRIPTION OF THE DRAWINGS

FIG. 2 illustrates general formulas for monomer and dimer prodrugs and precursors thereof.

DETAILED DESCRIPTION OF THE INVENTION

Figure 1:
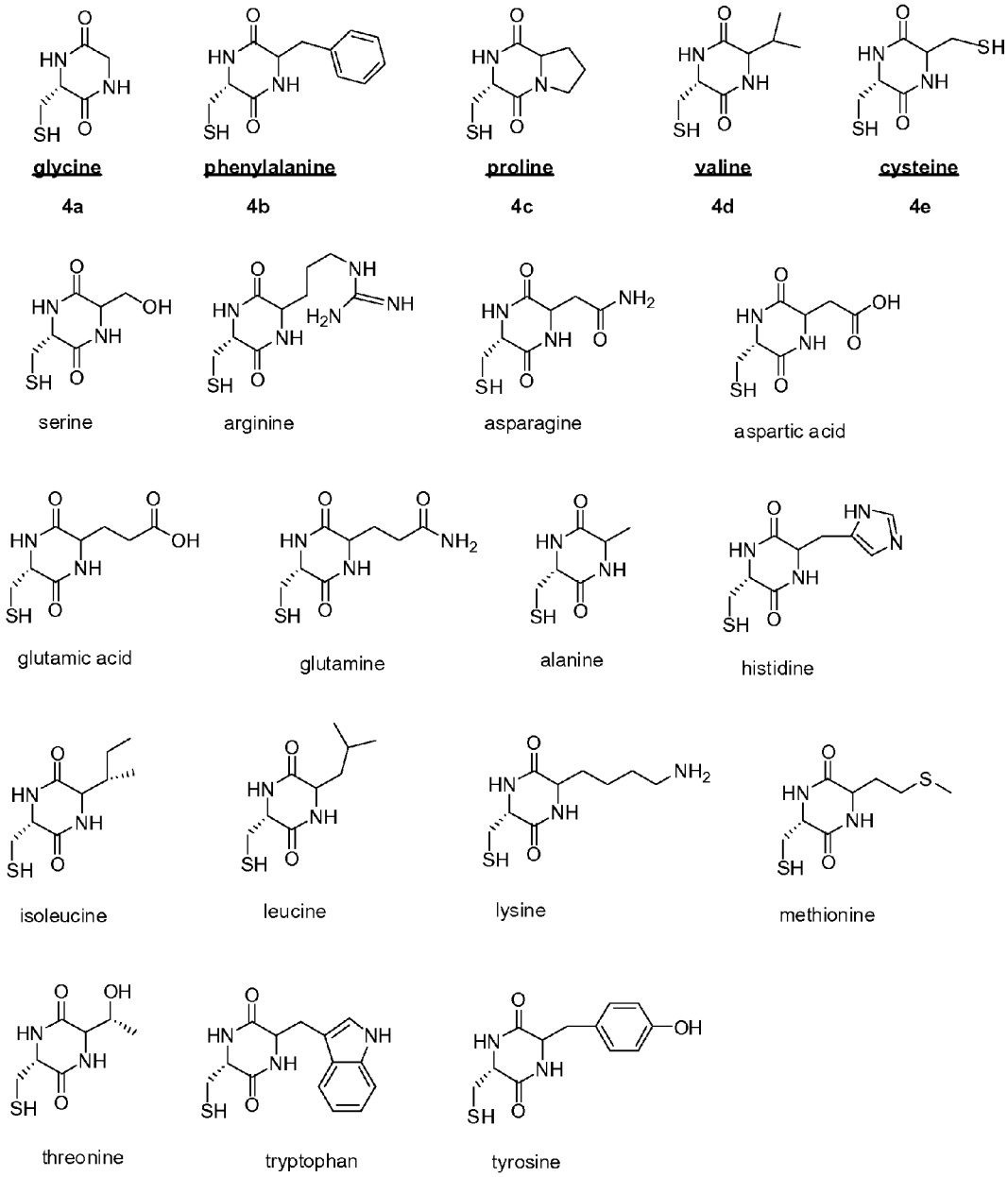
FIG. 1 depicts diketopiperazine targets based on various natural L-amino acids and D-isomers thereof.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The term "lower alkyl group(s)" as used herein indicates a linear, branched or cyclic alkyl group(s) having 1 to 6 carbon atoms. They include, for example, methyl group, ethyl group, n-propyl group, n-butyl group, n-pentyl group, n-hexyl group, isopropyl group, isobutyl group, sec-butyl group, tert-butyl group, isopentyl group, tert-pentyl group, neopentyl group, 2-pentyl group, 3-pentyl group, 3-hexyl group, 2-hexyl group, cyclopropyl group, cyclobutyl group, cyclopentyl group and cyclohexyl group. In them, methyl group, ethyl group, etc. are preferred.

The term "aryl group(s)" as used herein indicates a monocyclic or bicyclic aromatic substituent(s) composed of 5 to 12 carbon atoms, such as phenyl group, indenyl group, naphthyl group and fluorenyl group. In them, phenyl group is preferred. The term "arylthio group" indicates a monocyclic or bicyclic aromatic substituent(s) composed of 5 to 12 carbon atoms and further including a thio moiety.

The term "alkylthio group(s)" as used herein indicates an alkylthio group(s) having a linear, branched or cyclic alkyl group having 1 to 12 carbon atoms, preferably 1 to 5 carbon atoms, such as methylthio group, ethylthio group, n-propylthio group, isopropylthio group, n-butylthio group, isobutylthio group, sec-butylthio group, tert-butylthio group, cyclopropylthio group, cyclobutylthio group, cyclopentylthio group and cyclobutylthio group.

The term "acyl group(s)" as used herein indicates a formyl group, an acyl group(s) having a linear, branched or cyclic alkyl group having 1 to 6 carbon atoms, acyl group(s) having a linear, branched or cyclic alkenyl group having 1 to 6 carbon atoms, acyl group(s) having a linear, branched or cyclic alkynyl group having 1 to 6 carbon atoms or acyl group(s) having an aryl group which may be substituted, such as formyl group, acetyl group, propionyl group, butyryl group, isobutyryl group, valeryl group, isovaleryl group, pivaloyl group, hexanoyl group, acryloyl group, methacryloyl group, crotonoyl group, isocrotonoyl group, benzoyl group and naphthoyl group. Acyl groups having a heterocyclic ring can also be used, for example, furanyl carbonyl group, thienyl carbonyl group, isoxazolyl carbonyl group and thiazolyl carbonyl group.

The term "thio acyl group(s)" as used herein indicates a thio acyl group(s) having a linear, branched or cyclic alkyl group having 1 to 6 carbon atoms, thio acyl group(s) having a linear, branched or cyclic alkenyl group having 1 to 6 carbon atoms, thio acyl group(s) having a linear, branched or cyclic alkynyl group having 1 to 6 carbon atoms or thio acyl group(s) having an aryl group which may be substituted, such as formyl group, acetyl group, propionyl group, butyryl group, isobutyryl group, valeryl group, isovaleryl group, pivaloyl group, hexanoyl group, acryloyl group, methacryloyl group, crotonoyl group, isocrotonoyl group, benzoyl group and naphthoyl group. Thio acyl groups may be incorporated in a heterocyclic ring, for example, thienyl carbonyl group and thiazolyl carbonyl group.

The term "amino acid" refers to an organic acid containing an amino group. The term includes naturally occurring amino acids ("natural amino acids") such as alanine, valine, leucine, isoleucine, proline, phenylalanine, tryptophan, methionine, glycine, serine, threonine, cysteine, asparagine, glutamine, tyrosine, histidine, lysine, arginine, aspartic acid, and glutamic acid. Amino acids can be pure L or D isomers or mixtures of L and D isomers.

"Prodrugs" refers to compounds, including monomers and dimers of the compounds of the invention, which have cleavable groups and become under physiological conditions compounds which are pharmaceutically active in vivo.

"Subject" includes humans. The terms "human," "patient" and "subject" are used interchangeably herein.

"Therapeutically effective amount" means the amount of a compound that, when administered to a subject for treating a disease or disorder, is sufficient to effect such treatment for the disease or disorder. The "therapeutically effective amount" can vary depending on the compound, the disease or disorder and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

The present inventors have recently identified the cystine-glutamate antiporter as a highly novel cellular process that likely contributes to the pathology underlying schizophrenia. Importantly, the inventors have collected the first data set indicating that cysteine prodrugs, used to increase the activity of cystine-glutamate antiporters, block cognitive deficits and social withdrawal in the preclinical phencyclidine model of schizophrenia. Unlike existing medications, cysteine prodrugs appear to exert antipsychotic properties, in part, by reversing pathology underlying the disease.

While no one theory or mechanism of pharmacological effect is adopted herein, cysteine prodrugs appear to restore diminished signaling to glutamate receptors and diminished glutathione levels observed in schizophrenics. A depleted glutathione level can lead to increased oxidative stress, and impaired cystine-glutamate antiporter activity, glutamate neurotransmission, synaptic connection, and gene expression, all of which are observed in schizophrenia.

As a related matter, as made evident by the inventors' findings, impaired cystine-glutamate antiporter activity and faulty glutamate neurotransmission bear on the issue of uncontrolled drug use, i.e., drug addiction. Uncontrolled drug use and heightened susceptibility to relapse are defining features of addiction that contribute to the transition in drug consumption from a recreational to a compulsive pattern. Long-term plasticity resulting in augmented excitatory neurotransmission within corticostriatal pathways in response to drugs of abuse have been implicated in addiction. Human cocaine abusers exposed to craving-inducing stimuli exhibit increased activation of excitatory circuits originating in cortical regions, including orbital and prefrontal cortex, and projecting to the ventral striatum; further, the degree of activation of corticostriatal pathways correlates with craving in humans.

Preclinical data also indicate the existence of drug-induced plasticity leading to activation of corticostriatal pathways. Activation of these circuits results in heightened extracellular glutamate in the nucleus accumbens and stimulation of ionotropic glutamate receptors, both of which are necessary for cocaine primed reinstatement. Further, the dorsomedial prefrontal cortex has been shown to be necessary for reinstatement produced by exposure to drug-paired cues using the contextual reinstatement paradigm and in response to electrical foot shock. As a result, identification of cellular mechanisms capable of regulating synaptic glutamate represent targets in the treatment of addiction.

Increased excitatory neurotransmission in the nucleus accumbens may arise, in part, by diminished activity of cystine-glutamate antiporters. The recent data collected by the present inventors illustrates that glutamate released from these antiporters provides endogenous tonic stimulation to group II or 2/3 metabotropic glutamate receptors (mGluRs) and thereby regulates synaptic glutamate and dopamine release. Thus, altered glutamate signaling could arise as a consequence of decreased cystine-glutamate exchange. Repeated cocaine administration has been shown to blunt the activity of cystine-glutamate exchange, which likely contributes to a sequence of events, including diminished group II mGluR autoregulation and increased excitatory neurotransmission in the nucleus accumbens.

Cysteine prodrugs, such as N-acetylcysteine ("NAC"), are used to drive cystine-glutamate exchange by apparently elevating extracellular cystine levels, thereby creating a steep cystine concentration gradient. Preclinical studies have shown N-acetylcysteine to be effective in blocking compulsive drug-seeking in rodents. Further, extant clinical data also show a reduction in cocaine use and craving in cocaine abusers receiving NAC. Unfortunately, the full clinical efficacy of targeting cystine-glutamate exchange may be unrealized when utilizing NAC due to extensive first-pass metabolism and limited passive transport of this drug across the blood-brain barrier. The prodrugs described and claimed herein will not be significantly eliminated by the liver and will readily pass the blood-brain barrier. Cysteine is the reduced form of cystine and is readily oxidized in vivo to cystine, thus elevating either cysteine or cystine is believed to increase cystine-glutamate exchange.

The cysteine prodrug NAC has been previously shown to have a favorable safety/tolerability profile in human subjects. In fact, NAC has been used for decades in humans for other indications (e.g., as a mucolytic, acetaminophen toxicity) and as an experimental treatment (HIV, cancer) without producing severe adverse effects. However, NAC undergoes extensive first pass metabolism requiring the usage of high doses that limit the utility of the drug and, potentially, increase the chances of side effects due to the buildup of metabolized by-products. The chemical entities presently disclosed and claimed herein are designed to substantially avoid the problem of first pass metabolism and therefore exhibit increased efficacy as compared to prior cysteine prodrugs.

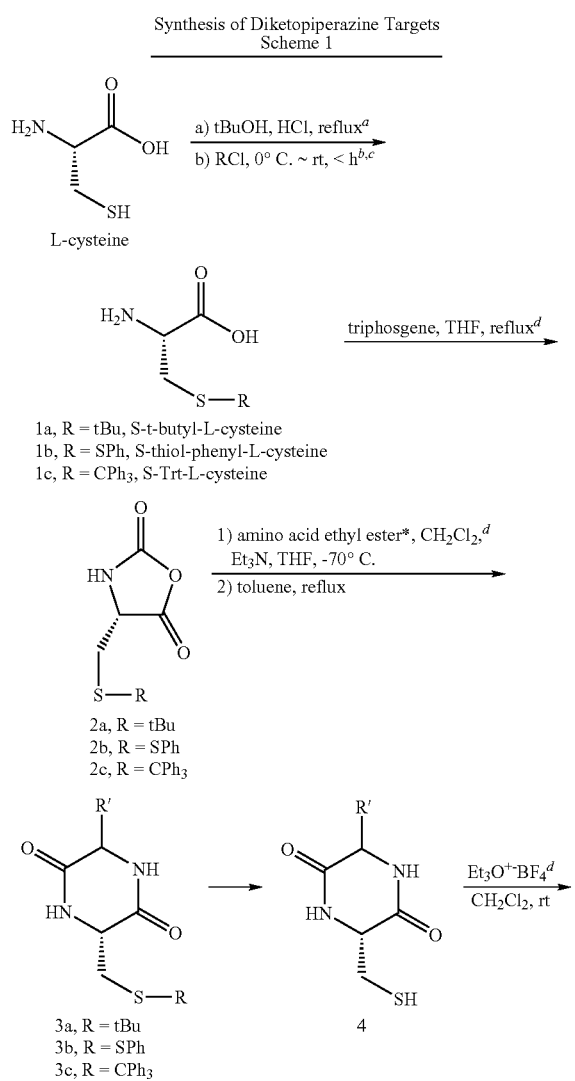

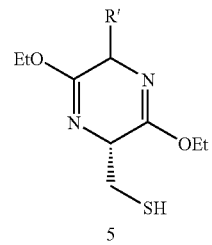

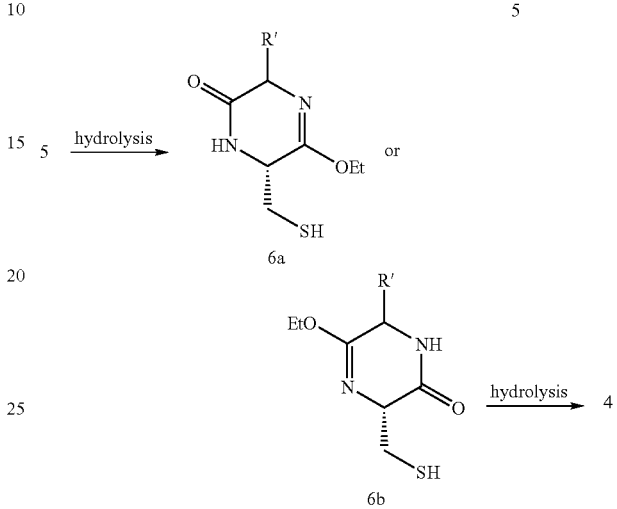

* all natural and selected unnatural amino acids will be used a) Pastuszak, J.J.; Chimiak, A.: tert-Butyl Group as Thiol Protection in Peptide Synthesis. *J. Org. Chem.* 46, 1868-1873 (1981). b) Sakakibara, S.; Tani, H. Synthesis of Polycysteine, *Bull. Chem Soc.* (Japan), 29, 85-88 (1956). c) Zervas, L.; Photaki, I. On Cysteine and Cystine Petides. I. New S-Protecting Groups for Cysteine. *J. Am. Chem. Soc.*, 84, 3887-3897 (1962). d) Zhao, S.; Liao, X.; Wang, T.; Flippen-Anderson, J.; Cook, J.M.; The Enantiospecific, Stereospecific Total Synthesis of the Ring-A Oxygenated Sarpagine Indole Alkaloids (+)-Majvinine, (+)-10-Methoxyaffinisine, and (+)-$N_a$-Methylsarpagine, and Well as the Total Syntheses of the Alstonia Bisindole Alkaloid Macralstonidine, *J. Org. Chem.*, 68, 6279-6295 (2003).

The preferred synthetic route to provide cysteine prodrugs according to the invention will now be described. Scheme 1 depicts the synthesis of the lead diketopiperazine targets 4 and 5. The chemistry employed is based on Schölkopf chiral auxiliary chemistry and provides yields on the kilogram scale. Protection of the thiol (—SH group) moiety in the cysteine is required to insure the formation of the Schölkopf chiral auxiliary and prevent other cyclization reactions. Thiol protection is accomplished by using either tert-butyl alcohol (in the presence of hydrochloric acid), phenylsulfenyl chloride or triphenyl methyl chloride (trityl chloride). Thiol protected cysteine is converted via 2, using the ethyl ester (methyl ester may also be used) of the desired amino acid, and undergoes intramolecular cyclization to produce the prodrug 3. Deprotection of the thiol group produces the lead diketopiperazine target 4.

Depicted in FIG. 1 are exemplary compounds that can be made using naturally occurring L-amino acids and D-isomers thereof. Alkylation of carboxyl groups on target 4 produces another prodrug 5 (Scheme 1). Furthermore, the dealkylation of the carboxyl group on 5 through hydrolysis provides prodrugs 6a and 6b and eventually 4.

The synthesis of the symmetrical cystine prodrugs is preferably accomplished by carrying out the thiol deprotection step in either a) ethanol with a catalytic amount of mercaptoethanol for the phenylsulfenyl protected thiol or b) pyridine using a catalytic amount of iodine for the triphenyl methane protected thiol, as shown in Scheme 2. However, the free thiol diketopiperazine can be used to produce symmetrical cystine prodrugs in ethanol and the presence of a catalytic amount of iodine. An exemplary cystine prodrug, the cysteine/glycine dimer, is further depicted in Scheme 2.

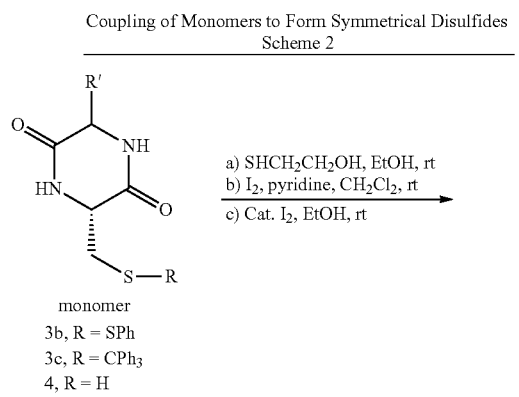

Coupling of Monomers to Form Symmetrical Disulfides
Scheme 2

The synthesis of hetero (unsymmetrical) disulfide dimers is preferably accomplished by using a one-pot reaction with 1-chlorobenzotriazole, as shown in Scheme 3. An alternate method involves using a catalytic amount of iodine in the presence of an equal molar amount of any two triphenyl methane protected thiol cysteine prodrugs. The desired target can be separated and purified using simple column chromatography.

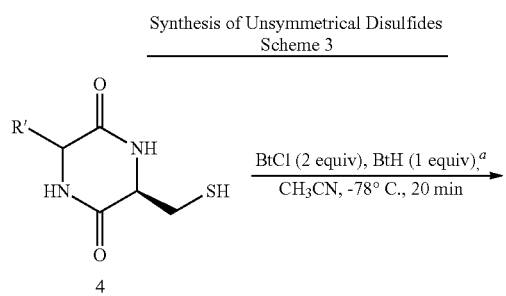

Synthesis of Unsymmetrical Disulfides
Scheme 3

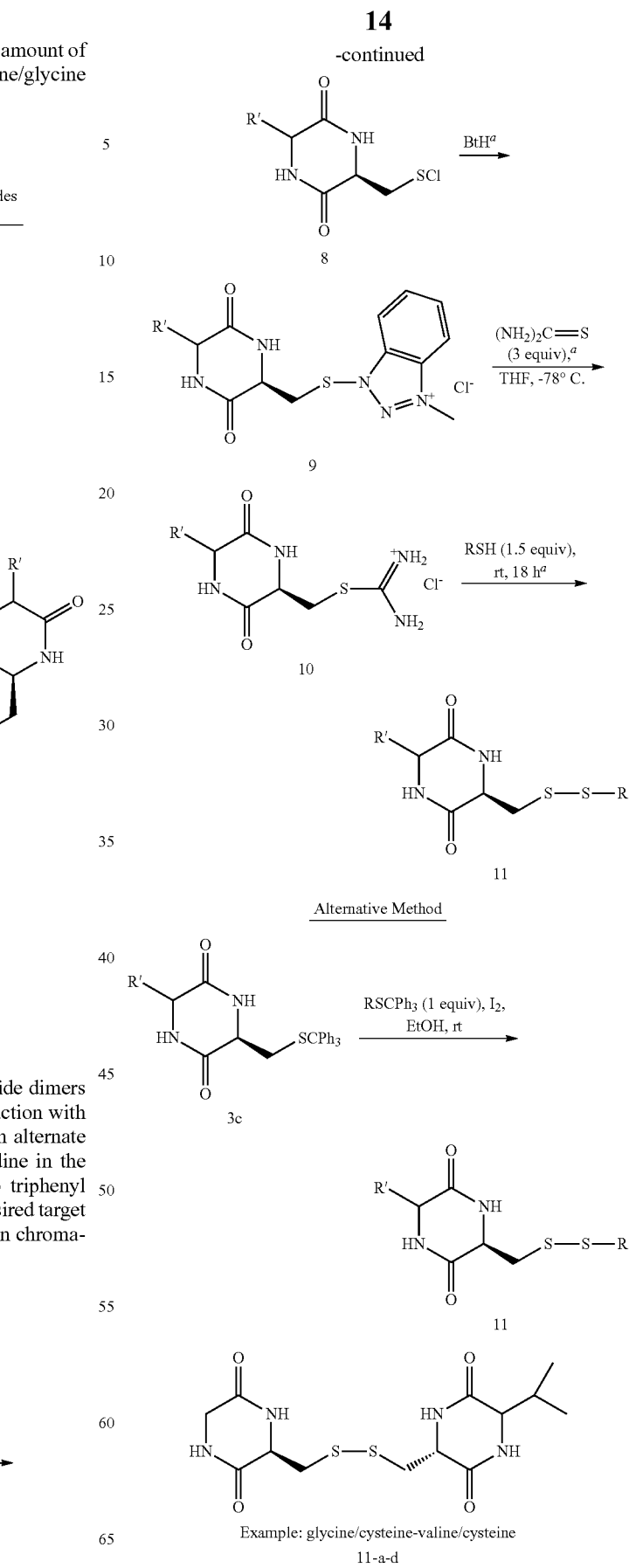

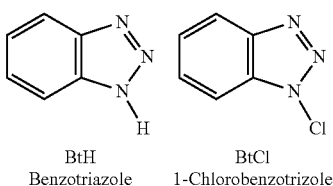

BtH
Benzotriazole

BtCl
1-Chlorobenzotrizole a) Hunter, R.; Caira, M.; Stellenboom, N.: Inexpensive, One-Pot Synthesis of Unsymmetrical Disulfides Using 1-Chlorobenzotriazole. *J. Org. Chem.* 71, 8268-8271 (2006).

Unsymmetrical disulfides can be synthesized from any two sulfide ligands provided by the above-described chemistries. Accordingly, the invention encompasses symmetrical and unsymmetrical disulfide dimers synthesized from the combination of any two sulfide monomers described herein.

The present method of synthesizing prodrugs according to the invention has many advantages over previous routes including, but not limited to: a) same synthetic route leads to both monomers and dimers (cysteine and cystine prodrugs); b) protection of the thiol group prevents side (cyclization) reactions; c) the initial monomer synthesis eliminates problems associated with multiple functional groups; d) the occurrence of undesired intramolecular and intermolecular side reactions is decreased; e) and the described route can be easily expanded to incorporate additional amino acids.

Particularly preferred cysteine monomers (prodrugs) according to the invention are shown in FIG. 1, boldfaced and underlined. These compounds are preferred either for advantages in partition coefficients (valine, proline), active transport (phenylalanine, proline), or breakdown products (cysteine, glycine). All targets synthesized from the diketopiperazine moiety are eventually cleaved and/or metabolized by either intra- or extra-cellular mechanisms to produce cysteine or cystine, which can then be used in the cystine-glutamate antiporter. FIG. 2 depicts general chemical formulas for certain cysteine and cystine prodrugs encompassed by the present invention.

Accordingly, the invention provides a cysteine prodrug having the structure:

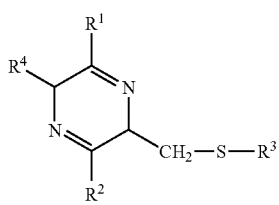

wherein: $R^1$ and $R^2$ are independently selected from OH, =O, or a branched or straight chain $C_1$ to $C_5$ alkoxyl group, with the caveat that when =O is selected the nitrogen atom adjacent the carbonyl group thusly formed bears a H and a single bond joins the adjacent nitrogen to said carbonyl group; $R^3$ is H, a branched or straight chain $C_1$ to $C_5$ alkyl, a nitrobenzenesulfonyl, a trityl, an aryl thio, an aryl, an alkylthio, an acyl, a benzoyl, a thio acyl, a thio benzoyl, or a benzyl group; and $R^4$ is selected from the side chain groups of the natural L-amino acids cys, gly, phe, pro, val, ser, arg, asp, asn, glu, gln, ala, his, ile, leu, lys, met, thr, trp, tyr, or D-isomers thereof, with the caveat that when $R^4$ is the side chain group of the natural L-amino acid gly, $R^1$ and $R^2$ are not both selected to be =O; or a cystine dimer of said prodrug having the structure:

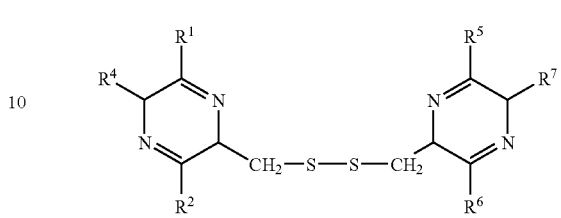

wherein: $R^1$, $R^2$, $R^5$ and $R^6$ are independently selected from OH, =O, or a branched or straight chain $C_1$ to $C_5$ alkoxyl group, with the caveat that when =O is selected the nitrogen atom adjacent the carbonyl group thusly formed bears a H and a single bond joins the adjacent nitrogen to said carbonyl group; and $R^4$ and $R^7$ are independently selected from the side chain groups of the natural L-amino acids cys, gly, phe, pro, val, ser, arg, asp, asn, glu, gln, ala, his, ile, leu, lys, met, thr, trp, tyr, or D-isomers thereof, with the caveat that when $R^4$ and $R^7$ are both the side chain group of the natural L-amino acid gly, $R^1$, $R^2$, $R^5$ and $R^6$ shall not all be selected to be =O.

In certain preferred embodiments, the cysteine prodrug according to the invention has the structure:

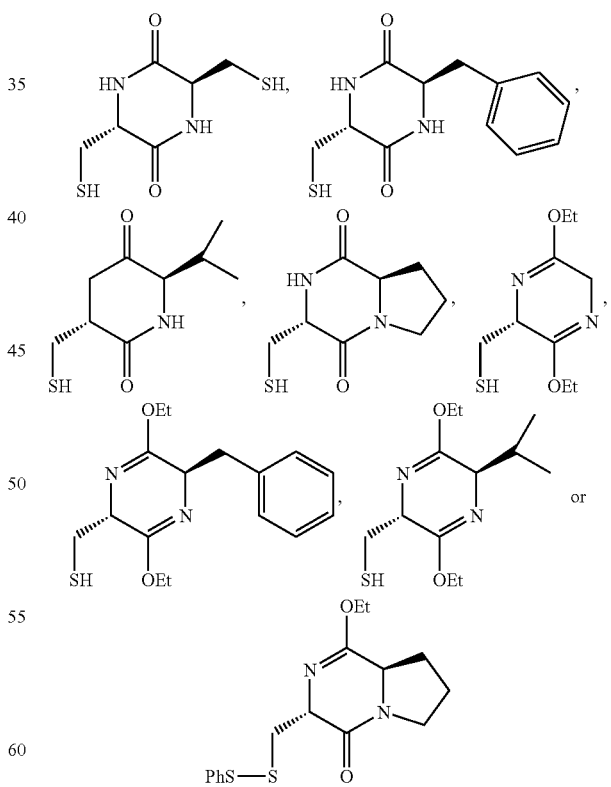

The cysteine prodrug may alternatively be provided in the form of a cystine dimer. Certain preferred cystine dimers according to the invention have the structure: the form of the cystine dimer having the structure:

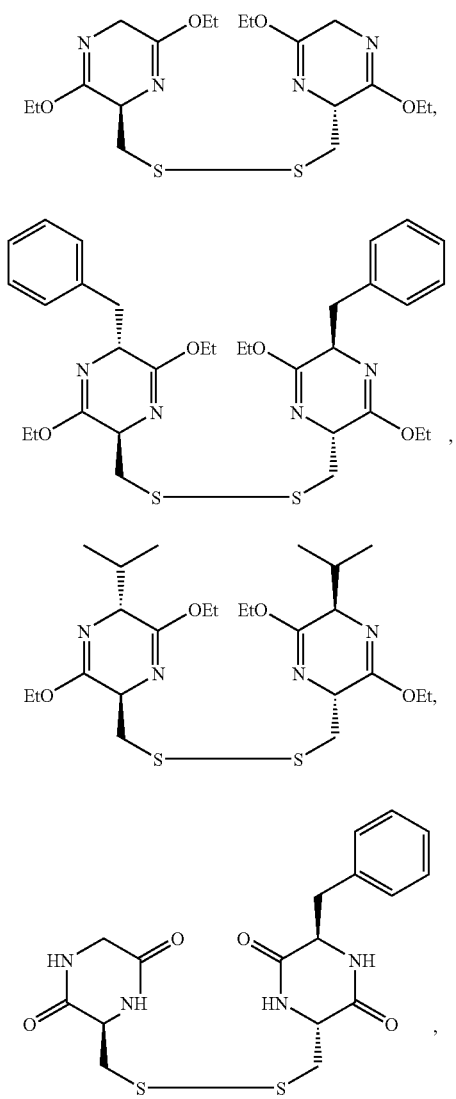

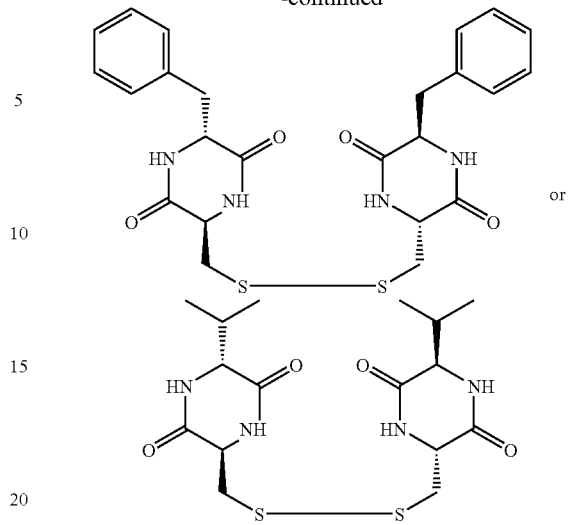

The invention provides synthetic routes for the synthesis of cystine dimers having identical $R^4$ and $R^7$ groups or, alternatively, mixed or non-identical $R^4$ and $R^7$ groups. Cystine dimers of the invention may therefore be of either symmetric or asymmetric design.

In certain cysteine prodrugs or cystine dimers of the invention, at least one $R^4$ or $R^7$ group is the side chain of cysteine and the reactive moiety thereof is further protected by a branched or straight chain $C_1$ to $C_5$ alkyl, a nitrobenzenesulfonyl, a trityl, an aryl thio, an aryl, an alkylthio, an acyl, a benzoyl, a thio acyl, a thio benzoyl, or a benzyl group.

Upon administration to a subject, compounds according to the invention pass largely intact through first pass metabolism and then are hydrolyzed (cleaved) into the corresponding amino acids by peptidases in cells contained within the CNS. Accordingly, prodrugs are chemical entities that are readily convertible in vivo to become pharmaceutically active.

Scheme 4 and Scheme 5 illustrate yet another approach provided by the invention in which L-cysteine is protected as acyl analogs with alkyl esters to improve the partition coefficient (Log P) and circulatory half life in the blood to provide improved passive delivery into the brain through the blood brain barrier.

Synthesis of Protected Analogs with Various Groups to Alter the Partition Coefficients
Scheme 4

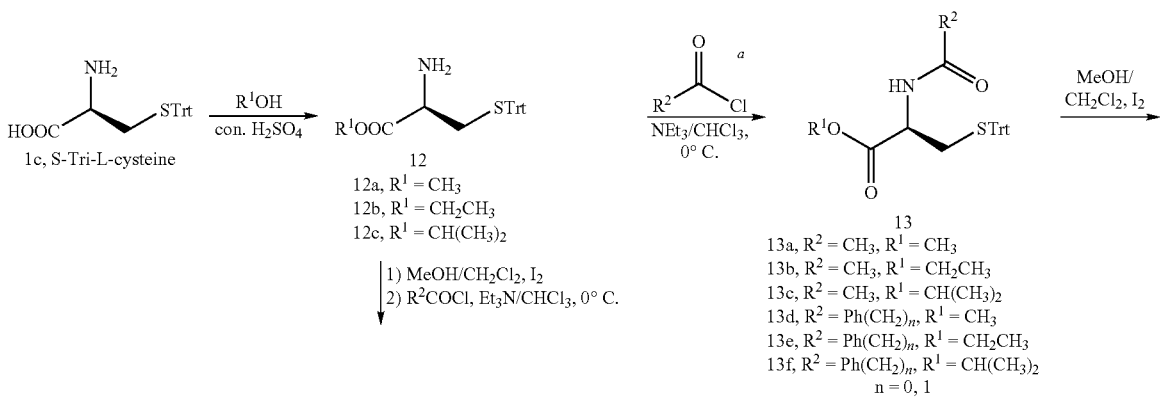

-continued

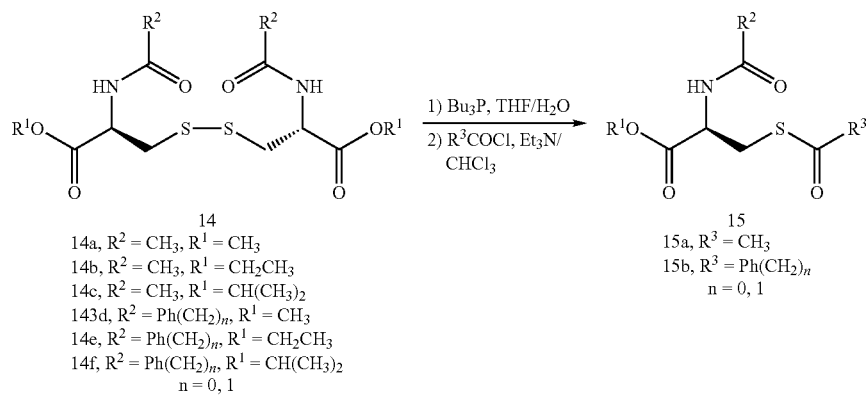

14
14a, $R^2 = CH_3$, $R^1 = CH_3$
14b, $R^2 = CH_3$, $R^1 = CH_2CH_3$
14c, $R^2 = CH_3$, $R^1 = CH(CH_3)_2$
143d, $R^2 = Ph(CH_2)_n$, $R^1 = CH_3$
14e, $R^2 = Ph(CH_2)_n$, $R^1 = CH_2CH_3$
14f, $R^2 = Ph(CH_2)_n$, $R^1 = CH(CH_3)_2$
n = 0, 1

15
15a, $R^3 = CH_3$
15b, $R^3 = Ph(CH_2)_n$
n = 0, 1

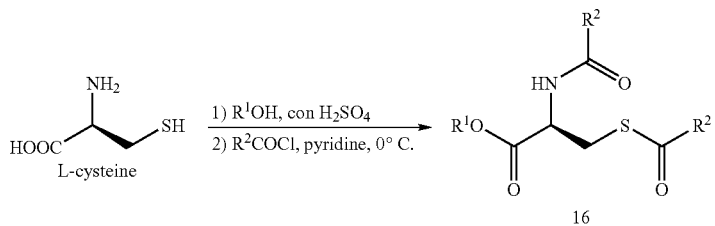

16 a) Shiina, I.; Kubota, M.; Oshiumi, H.; Hashizume, M.; An Effective Use of Benzoic Anhydride and Its Derviatives for the Synthesis of Carboxylic Esters and lactones: A Powerful and Convenient Mixed Anhydride Method Promoted by Basis Catalysts. *J. Org. Chem.*, 69, 1822-1830 (2004).

Figure 3:
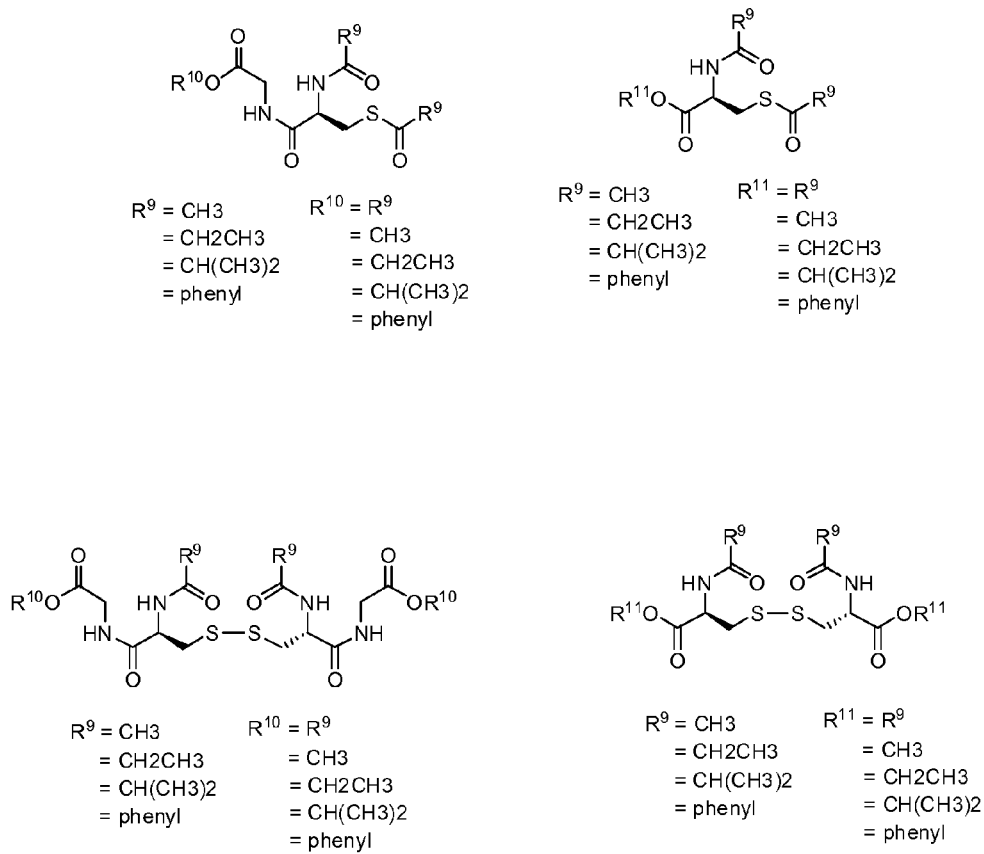
FIG. 3 provides general formulas for various protected cysteine analogs.

In Scheme 5, glycine is incorporated into some of the protected cysteine analogs (17) to provide a more efficient method of delivery of both amino acids. Various alkyl alcohols are incorporated into targets from Scheme 4 (12). Symmetrical cystine targets are synthesized from the corresponding cysteine analogs by the addition of a catalytic amount of iodine. Again, all prodrugs are hydrolyzed (cleaved) into the active corresponding amino acid in vivo. The molecules described in Scheme 4 and Scheme 5 result in more exposure and increased brain levels as compared to previous versions. It is noteworthy that this approach alters the partition coefficient by completely protecting the cysteine/cystine moiety. Synthetic challenges, such as solubility and stability of resulting intermediates and targets, have previously prevented others in the field from obtaining protected products in significant quantities, even for research studies. FIG. 3 depicts general chemical formulas for certain protected cysteine analogs encompassed by the present invention.

Synthesis of Protected Analogs with Glycine and Various Groups to Alter the partition Coefficients
Scheme 5

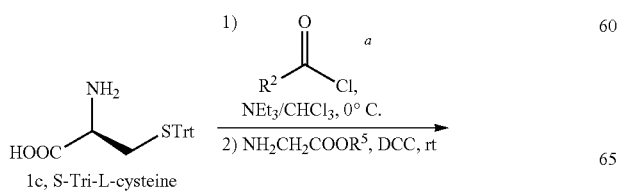

-continued

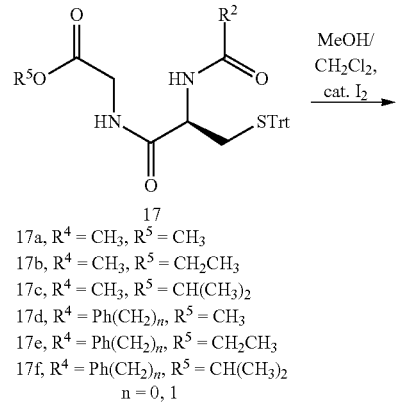

17
17a, $R^4 = CH_3$, $R^5 = CH_3$
17b, $R^4 = CH_3$, $R^5 = CH_2CH_3$
17c, $R^4 = CH_3$, $R^5 = CH(CH_3)_2$
17d, $R^4 = Ph(CH_2)_n$, $R^5 = CH_3$
17e, $R^4 = Ph(CH_2)_n$, $R^5 = CH_2CH_3$
17f, $R^4 = Ph(CH_2)_n$, $R^5 = CH(CH_3)_2$
n = 0, 1

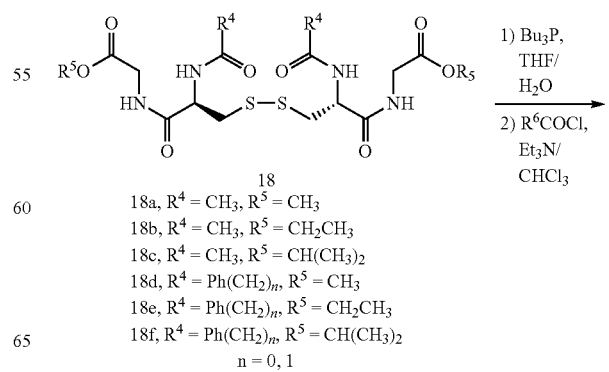

18
18a, $R^4 = CH_3$, $R^5 = CH_3$
18b, $R^4 = CH_3$, $R^5 = CH_2CH_3$
18c, $R^4 = CH_3$, $R^5 = CH(CH_3)_2$
18d, $R^4 = Ph(CH_2)_n$, $R^5 = CH_3$
18e, $R^4 = Ph(CH_2)_n$, $R^5 = CH_2CH_3$
18f, $R^4 = Ph(CH_2)_n$, $R^5 = CH(CH_3)_2$
n = 0, 1

-continued

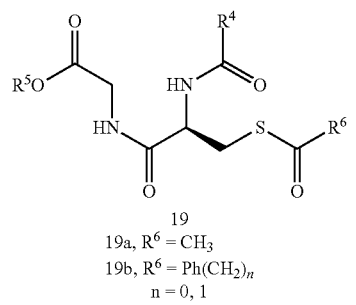

19
19a, R⁶ = CH₃
19b, R⁶ = Ph(CH₂)ₙ
n = 0, 1 a) Shiina, I.; Kubota, M.; Oshiumi, H.; Hashizume, M.; An Effective Use of Benzoic Anhydride and Its Derviatives for the Synthesis of Carboxylic Esters and Lactones: A Powerful and Convenient Mixed Anhydride Method Promoted by Basic Catalysts. *J. Org. Chem.*, 69, 1822-1830 (2004).

Accordingly, the invention further encompasses protected cysteine analogs having the structure:

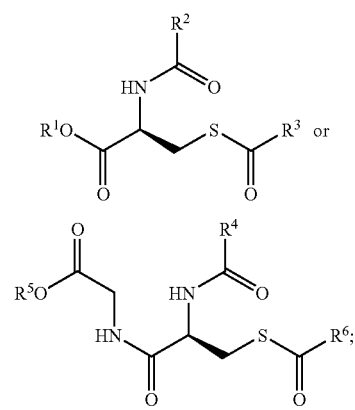

or a cystine dimer of the protected cysteine analog having the structure:

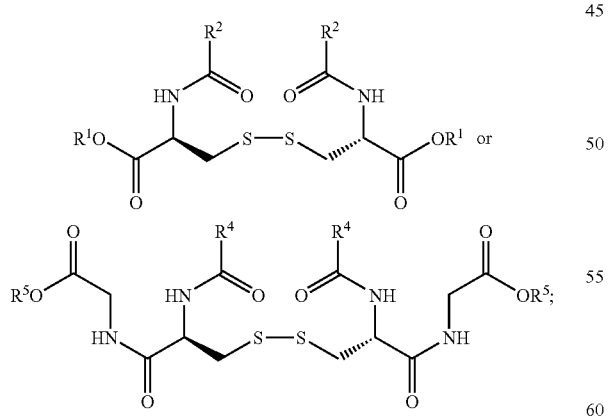

wherein $R^1$ through $R^6$ are independently selected from a branched or straight chain $C_1$ to $C_5$ alkyl, a phenyl, or a benzyl group.

Preferable protected cysteine analogs according to the invention have the structure:

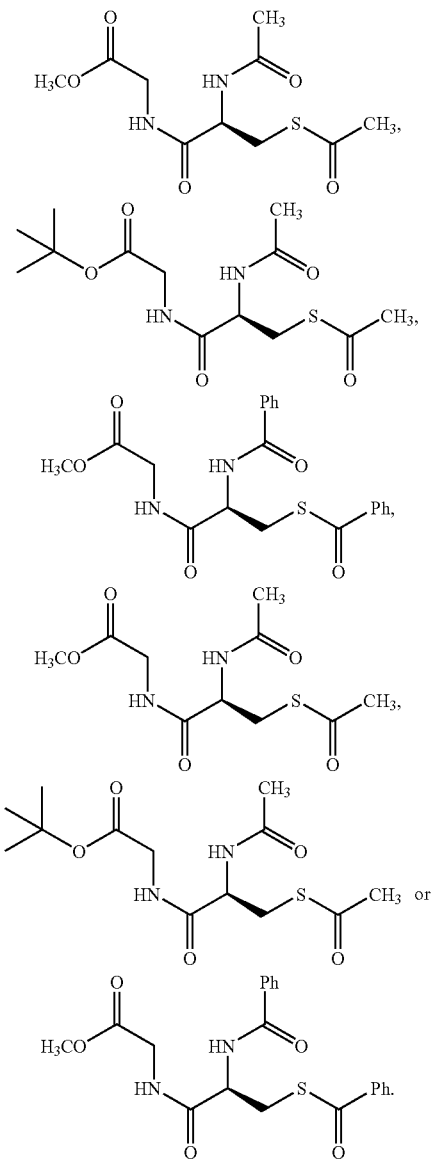

Alternatively, protected cysteine analogs may be provided in the form of the corresponding cystine dimers. Certain preferred cystine dimers have the structures:

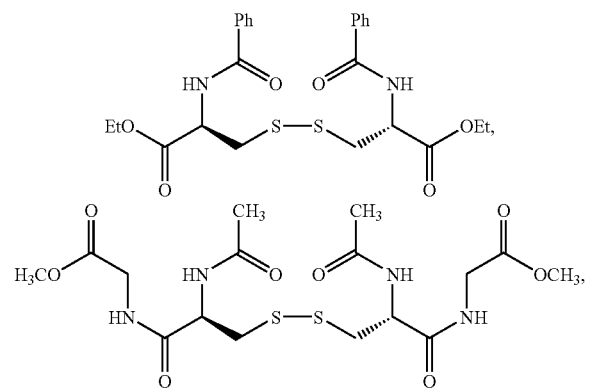

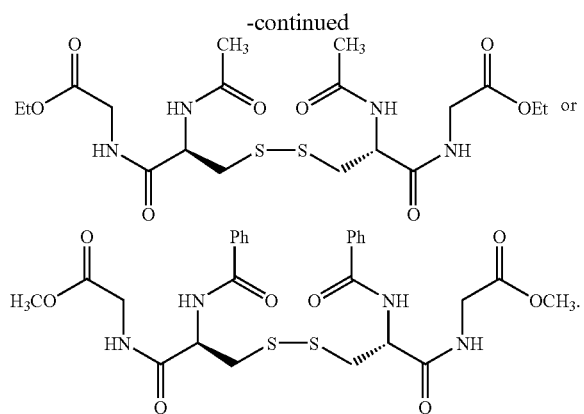

Relative to the protected cysteine analogs, the invention further provides a method of reducing schizophrenia in a subject by administering to a subject an effective amount of a protected cysteine analog or cystine dimer thereof according to the invention, whereby schizophrenia is reduced in said subject. Administration is preferably via the oral route.

Of course, the invention further encompasses pharmaceutical compositions containing a protected analog or dimer thereof in combination with a pharmaceutically-acceptable carrier. Methods of formulating/manufacturing such pharmaceutical compositions for the treatment of schizophrenia or for reducing drug craving in a subject are also within the invention's scope.

In certain preferred embodiments, the compounds of the invention will be provided as pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The compounds according to the present invention exhibit schizophrenia reducing/alleviating activity, as demonstrated by standard protocols. For example, efficacy of the present inventive compounds in the schizophrenia context has been demonstrated by assaying startle response to a load stimulus (pulse) when preceded by a pre-pulse stimulus. Accordingly, another aspect of the invention provides a method for the reduction of schizophrenia in a subject in need of such treatment by administration of an effective amount of compound according to the invention or a precursor thereof. In the treatment of schizophrenia, suitable dosage level (i.e, an effective amount) is about (1-5000) mg/kg, per day, preferably about (30-3000) mg/kg per day, and especially about (50-1000) mg/kg per day. The compounds may be administered on a regimen of 1 to 4 times per day, or on a continuous basis.

Accordingly, the present invention further provides a method of reducing schizophrenia in a subject. Such a method includes steps of administering to the subject an effective amount of a cysteine prodrug or cystine dimer thereof according to the invention, whereby schizophrenia is reduced in the subject. Administration is preferably accomplished by oral delivery.

As well, the compounds according to the present invention may also exhibit the ability to reduce drug cravings. This desirable activity can be shown in animal models involving drug-seeking behavior produced by stress, drug-paired cues, or a cocaine priming injection. Accordingly, yet another aspect of the invention is directed to a method of reducing a drug craving in a subject in need thereof. Such a method includes the step of administering an effective amount of a compound having the chemical structure of compound according to the invention, or a precursor thereof, to the subject whereby the drug craving is reduced in the subject. In the treatment of drug cravings, suitable dosage level (i.e., effective amount) is about (1-5000) mg/kg, per day, preferably about (30-3000) mg/kg per day, and especially about (50-1000) mg/kg per day.

The invention therefore provides a method of reducing drug craving in a subject. Such a method includes steps of administering to the subject an effective amount of a cysteine prodrug or cystine dimer of the invention, whereby drug craving is reduced in the subject. Again, administration is preferably via the oral route.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

In the following examples, the compounds where named based on the following criteria: Cysteine prodrugs (monomers) were assigned names as (Assigned number from Scheme—Amino acid incorporated; a=glycine, b=phenylalanine, c=proline, d=valine, e=cysteine) (i.e. 3c-a: Target 3c from Scheme 1 with glycine incorporated) or alternatively (Assigned number from Scheme with a "letter" indicating the amino acid incorporated) (i.e. 4a: Target 4 from Scheme 1 with glycine incorporated), Cystine prodrugs were named as (Assigned number from Scheme with a "letter" indicating the amino acid incorporated) (i.e. 7b: Target 7 from Scheme 2 with phenylalanine incorporated) or alternatively as (Assigned number from Scheme with a "letter" indicating the amino acid incorporated—dimer) (i.e. 5a-dimer: The dimer of Target 5 from Scheme 1 with glycine incorporated). Unsymmetrical Cystine prodrugs were named as (Assigned number from Scheme—Amino acid incorporated (monomer 1)—Amino acid incorporated (monomer 2)) (i.e. 11-a-b: Target 11 from Scheme 3 with glycine incorporated into monomer 1 and phenylalanine incorporated into monomer 2).

EXAMPLES

Example 1

Experimental for Scheme 1 Compounds

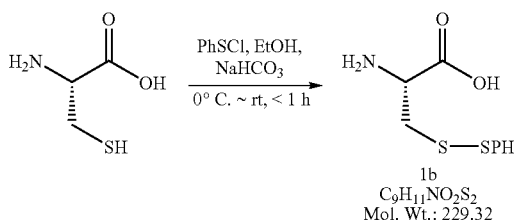

Preparation of p-Tolyl hypochlorothioite: Under a nitrogen atmosphere, N-chloro-succinimide (48.1 g, 0.36 mole) was slurried in 200 ml of methylene chloride. While stirring at room temperature, 4-methylbenzenethiol (29.8 g, 0.24 mole) was added; (2 g initial addition to start reflux and the remainder at a rate to maintain reflux approximate 10 min.) The clear solution which resulted was then stirred at room temperature for 30 minutes. A small amount of precipitate which formed was removed by filtration. The filtrate, assumed to contain the theoretical quantity of 4-methylbenzenesulfenyl chloride (38.1 g, 0.24 mole), was used immediately and directly in the next step. Alternatively, 4-methylbenzene-sulfenyl chloride was isolated by evaporation to an solid to its further use.

(R)-2-amino-3-(phenyldisulfanyl)propanoic acid (1b): To a solution of L-cysteine hydrochloride mono-hydrate (47 g, 0.3 mol) in absolute ethanol (900 mL) was added powdered sodium bicarbonate (30 g, 0.36 mol) at 0° C. in one portion. Phenylsulfenyl chloride (50 g, 0.345 mol) was added dropwise with stirring to the mixture. After the complete addition of the reagent, the reaction mixture was allowed to stand at room temperature and the sodium chloride which was produced during the reaction was removed by filtration. After basifying the mixture by the addition of pyridine (38 mL) into the filtrate, the fine precipitate which formed was allowed to stand for a couple of hours, then filtrated and washed well with ethanol and dried to provide the crude product as a white solid. After recrystallization from aqueous HCl (0.5 N, 4000 mL), the final product S-thiol-phenyl-L-cysteine (1b) was obtained (52 g) in 76% yield as colorless plates. 1b: m.p. 192° C. (decomp). $^1$H NMR (300 MHz, CD$_3$CO$_2$D): δ 3.53-3.76 (m, 2H), 4.89 (t, 1H), 7.26-7.88 (m, 5H); $^{13}$C NMR (75.5 MHz, CD$_3$CO$_2$D): δ 35.5, 52.5, 127.6, 128.5, 129.1, 129.3, 133.5, 171.6. This material was employed directly in the next step.

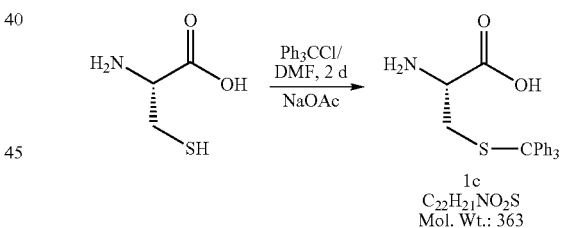

2-Amino-3-tritylsulfanyl-propionic acid (S-Trityl-L-cysteine) (1c): L-Cysteine hydro-chloride (100 g, 0.634 mol) and trityl chloride (270 g, 0.969 mol) were stirred in DMF (400 mL) for 2 days at room temperature. A 10% sodium acetate solution (3.5 L) was then added dropwise and the white precipitate which formed was filtered and washed with distilled water. Afterward, the residue was stirred in acetone at 50° C. for 30 min after which it was cooled to 0° C. and filtered. The precipitate was washed with a little acetone and diethyl ether and dried in vacuo. S-Trityl-L-cysteine 1c (205 g, 89%) was obtained as a white powder. 1c: m.p. 192° C. (decomp); $^1$H NMR (300 MHz, DMSO-d$_6$) δ 2.45 (dd, 1H, J=9 Hz, 12 Hz), 2.58 (dd, 1H, J=4.4 Hz, 12 Hz), 2.91 (m, 1H), 7.22-7.36 (m, 15H); $^{13}$C NMR (75.5 MHz, DMSO-d$_6$): δ 33.8, 53.7, 66.4, 127.1, 127.8, 128.1, 128.4, 129.5, 144.5, 168.4. This material was directly used in the next step without further purification.

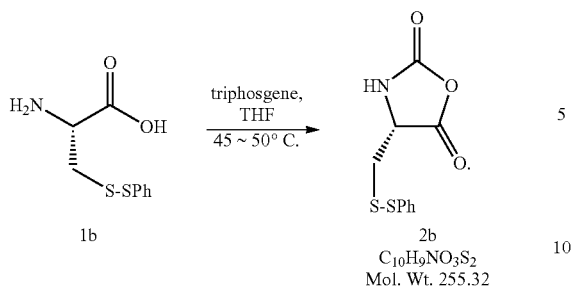

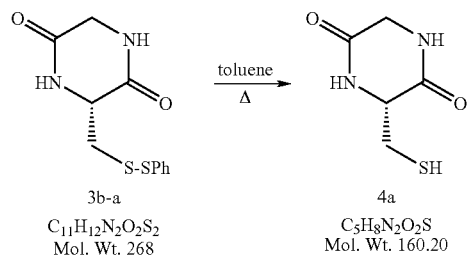

(R)-4-((phenyldisulfanyl)methyl)oxazolidine-2,5-dione (2b): To a rapidly stirred (over-head stirrer) suspension of S-thiol-phenyl-L-cysteine (1b) (57.5 g, 0.25 mol) in THF (250 mL) was added solid triphosgene (26 g, 88 mmol) in one portion at 45-50° C. (before addition, remove the heating mantle). When the temperature drops to 45° C., put the heating mantle back on and maintain the inside temperature around 45-50° C. until the solution becomes homogeneous. After the removal of the heating mantle, the solution was purged with argon overnight into a NaOH bubbler to remove any residual phosgene. The solvent was evaporated in vacuo and this provided anhydride 2b (55 g) in 85% yield. 2b: m.p. 217° C. (decomp); $^1$H NMR (300 MHz, CDCl$_3$) δ 2.90-2.98 (m, 1H), 3.30 (d, 1H, J=12 Hz), 4.68 (d, 1H, J=9 Hz), 6.01 (s, 1H), 7.34-7.58 (m, 5H); $^{13}$C NMR (75.5 MHz, CD$_3$Cl$_3$): δ 39.4, 56.5, 128.3, 128.9, 129.5, 135.2, 150.8, 167.7. Due to the unstable nature of this anhydride, it was stored in the refrigerator overnight under an atmosphere of argon and used immediately the next day without further purification.

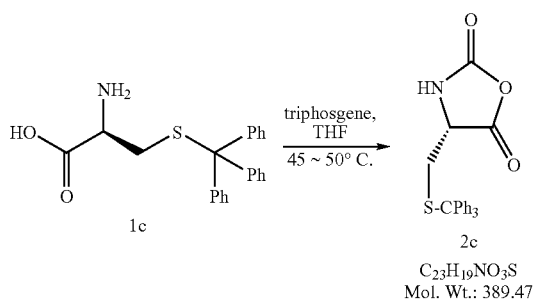

4-Tritylsulfanylmethyl-oxazolidine-2,5-dione (2c) was prepared following the procedure for preparation of 2b as a brown oil in 85% yield. 2c: $^1$H NMR (300 MHz, CDCl$_3$) δ 2.70-2.85 (m, 2H), 3.47-3.56 (m, 1H), 5.62 (s, 1H), 7.07-7.73 (m, 15H). This material was directly used in the next step without further purification.

Representative Procedure for Synthesis of Diketopiperazine Targets:

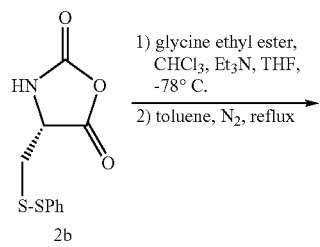

2,5-Piperazinedione, 3-(mercaptomethyl)-(4a): a). A solution of the N-carboxy-anhydride 2b (35.7 g, 0.14 mol) in THF (160 mL) was added dropwise to a vigorously stirred (over-head stirrer) mixture of glycine ethyl ester hydrochloride (28 g, 0.16 mol), freshly distilled triethylamine (20.4 g, ~28 mL, 0.20 mol) and dry chloroform (240 mL) at −78° C. in a three-neck flask (2 L). The reaction mixture was allowed to warm to 0° C. over 8 h, and then was stirred at rt for 12 h, after which the reaction solution was filtered to remove the triethylamine hydrochloride which precipitated. The filtrate was then concentrated under reduced pressure (<40° C.) and the crude dipeptide ester was used for the preparation of the diketopiperazine 4a without further purification. $^1$H NMR (300 MHz, CDCl$_3$): δ 1.29 (t, 3H), 1.93 (br, 2H), 2.74-2.82 (m, 1H), 3.40 (dd, 1H), 3.73 (dd, 1H), 4.03-4.19 (m, 2H), 4.19-4.26 (m, 2H), 7.34-7.58 (m, 5H). b). The crude dipeptide ester (37.6 g, 0.12 mol) was heated in refluxing toluene (1000 mL) for 12 h and then cooled down to rt and kept at 0° C. for 16 h. The bislactam 4a which precipitated was isolated by vacuum filtration, washed with ether (3×150 mL), and dried under vacuum at 100° C. to provide pure diketopiperazine 4a (10.0 g) in 45% yield. The resulting filtrate produced from washing the desired diketopiperazine was evaporated under vacuum and toluene (800 mL) was added to the residue. The toluene solution was heated at reflux for another 40 h (under argon) and then the above steps were repeated to collect another 5-8 grams of diketopiperazine 4a (combined yield, 73%). 4a: m.p. 258° C.; $^1$H NMR (300 MHz, DMSO-d$_6$): δ 3.09-3.26 (m, 2H), 3.68-3.88 (m, 2H), 4.10 (s, 1H), 8.17 (s, 1H), 8.19 (s, 1H); $^{13}$C NMR (500 MHz, DMSO-d$_6$): δ 43.5, 44.7, 54.3, 166.2, 166.6; EIMS (m/e, relative intensity) 160 (M$^+$, 12), 140(5), 126(72), 114(100), 97(20), 85(30).

3-Phenyldisulfanylmethyl-piperazine-2,5-dione (3b-a): c). The solution which resulted from step b above was cooled to 0° C. and keep at 0° C. for 12 h. The precipitate which resulted was filtered and provided phenyl-thiol analog 3b-a in 30% yield. 3b-a: $^1$H NMR (300 MHz, DMSO-d$_6$): δ 3.09-3.21 (m, 2H), 3.65-3.82 (m, 2H), 4.10 (s, 1H), 7.11-7.55 (m, 5H), 8.18 (s, 1H), 8.20 (s, 1H); $^{13}$C NMR (75.5 MHz, DMSO-d$_6$): δ 43.5, 47.8, 54.2, 125.6, 127.7, 128.2, 129.5, 166.2, 166.6; EIMS (m/e, relative intensity) 268 (M$^+$, 55), 250(35), 218(68), 159(66), 141(80), 126(70).

4b

C₁₂H₁₄N₂O₂S
Mol. Wt. 250

(3R,6R)-3-benzyl-6-(mercaptomethyl)piperazine-2,5-dione (4b): was prepared in 75% yield following the procedure for preparation of 4a and obtained as a light yellow solid. 4b: m.p. >265° C. (decomp.); $^1$H NMR (300 MHz, DMSO-d$_6$) δ 1.26 (d, J=6.99 Hz, 1H), 3.05-3.49 (m, 2H), 3.66-3.89 (m, 3H), 4.10 (s, 1H), 7.13-7.31 (m, 5H), 8.23 (s, 1H), 8.28 (s, 1H); $^{13}$C NMR (75.5 MHz, CDCl$_3$) δ 19.0, 37.9, 44.7, 48.1, 51.2, 54.4, 126.5, 129.1, 129.4, 165.9, 166.5. EIMS (m/e, relative intensity) 250 (M$^+$, 10), 216(12), 160(5), 113(11), 91(100).

4d

C₈H₁₄N₂O₂S
Mol. Wt. 202

(6R)-3-isopropyl-6-(mercaptomethyl)piperazine-2,5-dione (4d): was prepared in 74% yield following the procedure for preparation of 4a and obtained as a white solid. 4d: m.p. >275° C.; $^1$H NMR (300 MHz, DMSO-d$_6$) δ 0.84 (dd, J=7.14, 6.63 Hz, 3H), 0.94 (dd, J=8.07, 6.9 Hz, 3H), 2.17-2.20 (m, 1H), 3.07-3.18 (m, 2H), 3.73 (s, 1H), 4.22 (s, 1H), 8.12 (s, 1H), 8.18s (s, 1H); $^{13}$C NMR (75.5 MHz, CDCl$_3$) δ 17.5, 18.8, 42.9, 53.9, 59.7, 166.7, 167.2; HRMS m/z C₁₀H₁₈N₂O₂S₂(M−H)$^+$ calcd 201.0698, found 201.0691.

4e

C₁₀H₁₈N₂O₂S₂
Mol. Wt. 262

(6R)-3-(tert-butylthiomethyl)-6-(mercaptomethyl)piperazine-2,5-dione (4e): was prepared in 70% yield following the procedure for preparation of 4a and obtained as a yellow solid. 4e: m.p. >280° C. (decomp.); $^1$H NMR (300 MHz, DMSO-d$_6$) δ 1.25 (s, 9H), 2.88-2.92 (m, 1H), 3.03-3.10 (q, J=7.5 Hz, 1H), 3.18-3.21 (m, 1H), 3.51 (d, J=14.4 Hz, 1H), 4.14 (s, 2H), 8.13 (s, 1H), 8.24 (s, 1H); $^{13}$C NMR (75.5 MHz, CDCl$_3$) δ 31.1, 32.1, 43.2, 47.8, 54.1, 54.9, 166.3, 170.8; EIMS (m/e, relative intensity) 262 (M$^+$, 30), 228(40), 206 (45), 173(50), 160(70), 126(100); HRMS m/z C₁₀H₁₈N₂O₂S₂ (M+H)$^+$ calcd 263.0482, found 263.0489.

3b-c

C₁₄H₁₆N₂O₂S₂
Mol. Wt. 308

(3R,8aR)-3-((phenyldisulfanyl)methyl)hexahydropyrrolo[1,2-a]pyrazine-1,4-dione (3b-c) was prepared in 82% yield following the procedure for preparation of 3b-a and obtained as a yellow solid. 3b-c: m.p. 120° C.; $^1$H NMR (300 MHz, CDCl$_3$) δ 1.66-2.02 (m, 1H), 2.03-2.11 (m, 2H), 2.36 (m, 1H), 2.80-2.89 (m, 1H), 3.54-3.62 (m, 3H), 4.07-4.10 (m, 1H), 4.39 (dd, J=1.83, 1.77 Hz, 1H), 6.35 (s, 1H), 7.28-7.57 (m, 5H); $^{13}$C NMR (75.5 MHz, CDCl$_3$) δ 22.5, 28.2, 38.5, 45.4, 53.3, 59.1, 127.8, 128.6, 129.2, 135.6, 164.3, 169.0.

3c-a

C₂₄H₂₂N₂O₂S
Mol. Wt.: 402.51

3-Tritylsulfanylmethyl-piperazine-2,5-dione (3c-a) was prepared following the similar procedure for preparation of 4a. 3c-a: m.p. 225-227° C. [α]$_D^{26}$=+7.8° (c=1.05, CHCl$_3$). $^1$H NMR (300 MHz, CDCl$_3$) δ 2.73-2.91 (m, 2H), 3.12 (d, 1H, J=12.3 Hz), 3.95 (s, 1H), 5.80 (s, 1H), 5.82 (s, 1H), 7.20-7.62 (m, 15H). $^{13}$C NMR (75.5 MHz, CDCl$_3$): δ 35.9, 44.8, 53.0, 126.9, 128.1, 129.4, 144.0, 166.6. This material was directly used in the next step without further purification.

Representative Procedure for Synthesis of Dialkylated Diketopiperazine:

5a

C₉H₁₆N₂O₂S
Mol. Wt.: 216.30

(3,6-Diethoxy-2,5-dihydro-,pyrazin-2-yl)-methanethiol (5a)
Preparation of Triethyloxonium Tetrafluoroborate: (Note: Triethyloxonium tetra-fluoroborate is an expensive reagent;

however, it is relatively easy to prepare even on large scale). A three-neck flask (500 mL), pressure equilibrating dropping funnel (125 mL) and a condenser were dried in an oven at 150° C. and assembled while hot under an atmosphere of argon. When the equipment had cooled to rt, ether [(100 mL) which had been previously dried over sodium benzophenone ketyl] and boron trifluoride diethyletherate (91 g, ~87 mL, 64 mmol) were combined [Note: On this scale the colorless BF$_3$ etherate was obtained from a freshly opened new bottle. If the reagent was slightly yellow or if the reaction was scaled down, the BF$_3$ etherate needed to be vacuum distilled first]. The ethereal solution which resulted was heated to a gentle reflux after which dry epichlorohydrin (48.8 g, ~41 mL, 51.8 mmol) was added dropwise over 1 h. The mixture was heated at reflux for an additional 1 h and allowed to stand at rt (under argon) overnight. The ether was removed by applying a positive pressure of argon in one neck of the flask while forcing the ether out through a filter stick (fritted glass tube) inserted into another neck of the flask and into a collection flask. The slightly yellow solid which remained in the flask was rinsed twice in the same manner with anhydrous ether (3×50 mL) to provide a crystalline white solid. The solid was not weighed but directly used in the next step. The following sequence was based on the yield of this reaction process at the level of 80-85%.

Dry CH$_2$Cl$_2$ (100 mL) was added to the flask (500 mL) which contained the freshly prepared triethyloxonium tetrafluoroborate (~42 g, 336 mmol) from the previous reaction (under argon). To this solution was added the diketopiperazine 4a (5 g, 31.2 mmol) in portions with stirring (overhead stirrer). After 2 h the reaction mixture became homogenous. The solution was stirred at rt under argon for 72 h after which the mixture was added via a cannula to an aq solution of NH$_4$OH (14%, 100 mL) mixed with ice (100 g). The organic layer was washed with a saturated aq solution of NaHCO$_3$ (2×50 mL) and brine (80 mL) after which it was dried (K$_2$CO$_3$). After filtration the solvent was removed under reduced pressure to provide the bis-ethoxy lactim ether 5a as a clear yellow liquid that was further purified by flash chromatography (EtOAc:Hexane=1:4) in 71% yield (4.8 g, 22 mmol). 5a: [α]$_D^{26}$=+52.2° (c=2.5, CHCl$_3$). $^1$H NMR (300 MHz, CDCl$_3$) δ 1.32-1.36 (m, 6H), 3.27-3.30 (m, 3H), 4.08-4.22 (m, 6H), 4.39 (s, 1H); $^{13}$C NMR (75.5 MHz, CDCl$_3$): δ 14.7, 46.3, 47.5, 56.1, 61.5, 61.6, 162.7, 163.6; HRMS m/z C$_9$H$_{16}$N$_2$O$_2$S (M+H)$^+$ calcd. 217.2982, found 217.2990.

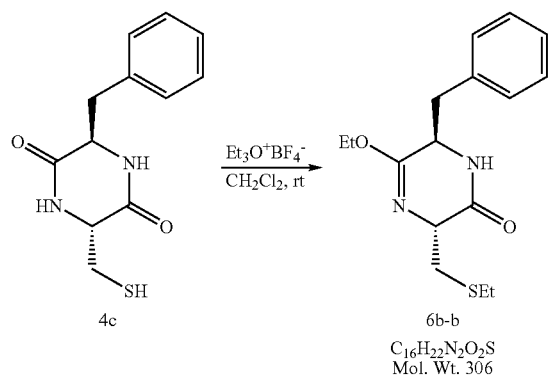

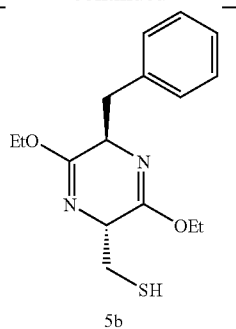

(3R,6R)-6-Benzyl-5-ethoxy-3-(ethylthiomethyl)-1,6-dihydropyrazin-2(3H)-one (6b-b) was prepared in 30% yield following the procedure for preparation of 5b using only 1 equiv. of triethyloxonium tetrafluoroborate and obtained as a yellow solid. 6b-b: m.p. 118° C.; $^1$H NMR (300 MHz, CDCl$_3$) δ 1.19 (t, J=7.41 Hz, 3H), 1.30 (t, J=7.08 Hz, 3H), 2.37-2.45 (m, 3H), 2.82-3.01 (m, 1H), 2.95 (d, J=3.09 Hz, 1H), 3.03 (d, J=3.12 Hz, 1H), 3.23 (q, J=32.6, 5.1 Hz, 2H), 4.14-4.19 (m, 2H), 4.46-4.47 (m, 1H), 6.19 (s, 1H), 7.17-7.29 (m, 5H); $^{13}$C NMR (75.5 MHz, CDCl$_3$): δ 14.1, 14.5, 25.7, 35.4, 39.8, 50.6, 60.0, 61.6, 126.5, 127.8, 130.2, 136.7, 157.8, 170.1; HRMS m/z (M+H)$^+$ calcd. 305.1515, found 305.1522.

Example 2

Representative Procedure for Synthesis of Bis-Dipiperazinedione

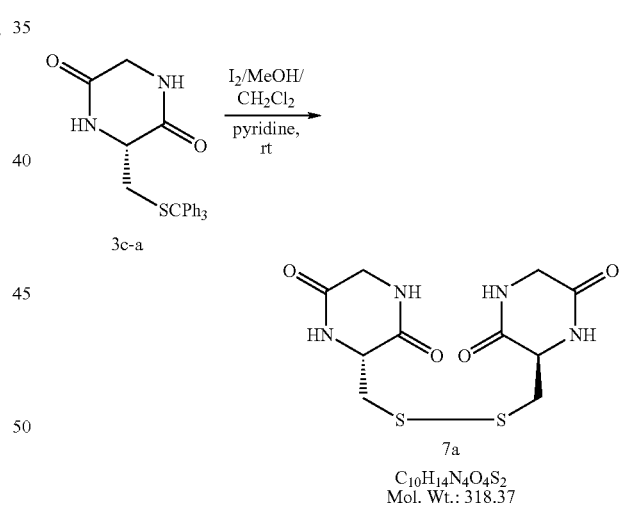

Bis[2,5-Piperazinedione, 3-(mercaptomethyl)-] (7a): The trityl protected diketo-piperazine 3c-a (1.5 g, 3.73 mmol) was dissolved in a solution of methylene chloride (20 mL) and methanol (40 mL) with stirring. Pyridine (1.2 mL, 15 mmol) was then added to the resulting mixture, followed by a solution of iodine (0.97 g, 3.8 mmol) in methanol (5 mL). The mixture was allowed to stir for 1 h at room temperature. No precipitate had formed by this time; however, TLC analysis indicated that the reaction was proceeding slowly by the appearance of a new spot under the starting material (UV light). A precipitate began to form within 2 h after concentrating the solution to a volume of 10 mL and methanol (30 mL) was added to result in a total volume of 40 mL. The solution was stirred an additional 23 h and the precipitate was filtered off. The solid was washed with cold methanol and then decolorized by shaking with 10% aqueous sodium bisulfite (10 mL). The precipitate was filtered and dried to yield dimer 7a as white solid (680 mg, 57%). 7a: m.p. >300° C. $^1$H NMR (300 MHz' DMSO-$d_6$) δ 3.11-3.21 (m, 2H), 3.70 (d, 1H, J=0.96 Hz), 3.73 (d, 1H, J=0.99 Hz), 4.11 (s, 1H), 8.17 (s, 1H), 8.19 (s, 1H); $^{13}$C NMR (75.5 MHz, DMSO-$d_6$): δ 44.0, 45.2, 54.8, 166.7, 167.1; HRMS m/z (M+H)$^+$ calcd. 319.0535, found 319.0533.

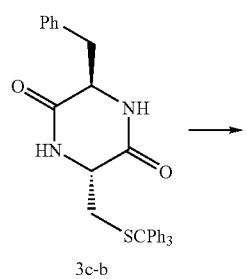

3c-b

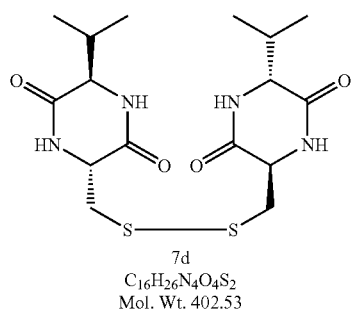

7d
$C_{16}H_{26}N_4O_4S_2$
Mol. Wt. 402.53

(3R,3'R,6R,6'R)-6,6'-disulfanediylbis(methylene)bis(3-isopropylpiperazine-2,5-dione) (7d): was prepared in 65% yield following the procedure for preparation of 7a and obtained as a white solid. 7d: m.p. 270° C.; $^1$H NMR (300 MHz, CDCl$_3$) δ 0.86 (d, J=6.75 Hz, 3H), 0.96 (d, J=7.05 Hz, 3H), 2.17-2.21 (m, 1H), 3.07-3.19 (m, 2H), 3.72 (s, 1h), 4.33 (s, 1H), 8.11 (s, 1H), 8.17 (s, 1H); $^{13}$C NMR (75.5 MHz, CDCl$_3$): δ 17.5, 18.8, 31.4, 42.9, 53.9, 59.7, 166.7, 167.2; HRMS m/z (M+H)$^+$ calcd. 403.1474, found 403.1479.

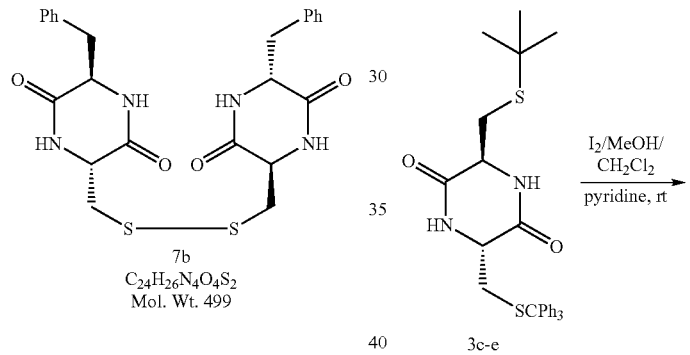

7b
$C_{24}H_{26}N_4O_4S_2$
Mol. Wt. 499

3c-e (3S,6S)-3-Benzyl-6-(((((2R,5R)-5-benzyl-3,6-dioxopiperazin-2-yl)methyl)disulfanyl)methyl)piperazine-2,5-dione (7b): was prepared in 63% yield following the procedure for preparation of 7a and obtained as a yellow solid. 7b: m.p. >280° C. (decomp.); $^1$H NMR (300 MHz, CDCl$_3$) δ 1.29 (s, 9H), 2.85-2.92 (m, 2H), 3.10-3.13 (m, 2H), 4.14 (s, 2H), 8.12 (s, 2H); $^{13}$C NMR (75.5 MHz, CDCl$_3$): δ31.1, 32.1, 42.5, 43.2, 53.9, 54.1, 166.2, 166.3.

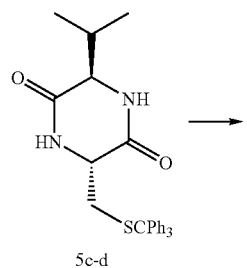

5c-d

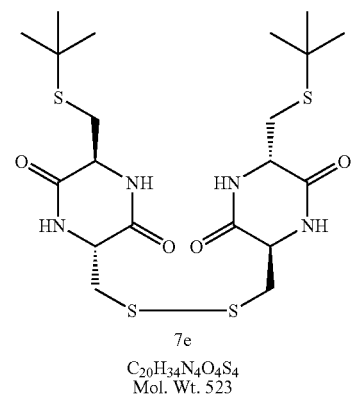

7e
$C_{20}H_{34}N_4O_4S_4$
Mol. Wt. 523

(3R,6S)-3-(tert-Butylthiomethyl)-6-(((((2R,5S)-5-(tert-butylthiomethyl)-3,6-dioxo-piperazin-2-yl)methyl)disulfanyl)methyl)piperazine-2,5-dione (7e): was prepared in 65% yield following the procedure for preparation of 7a and obtained as a yellow solid. 7e: m.p. 278° C.; $^1$H NMR (300 MHz, CDCl$_3$) δ 1.29 (s, 9H), 2.85-2.92 (m, 2H), 3.10-3.13 (m, 2H), 4.14 (s, 2H), 8.12 (s, 2H); $^{13}$C NMR (75.5 MHz, CDCl$_3$): δ 31.1, 32.1, 42.5, 43.2, 53.9, 54.1, 166.2, 166.3.

Representative Procedure for Synthesis of Bis[(3,6-Diethoxy-2,5-dihy-dro-pyrazin-2-yl)-methanethiol] (5a-dimer):

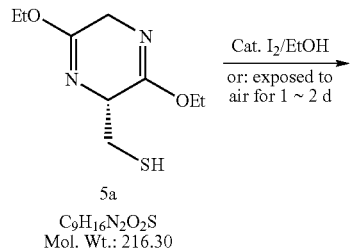

5a
$C_9H_{16}N_2O_2S$
Mol. Wt.: 216.30

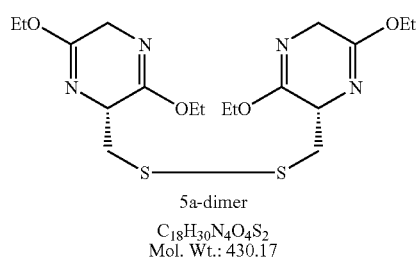

5a-dimer
$C_{18}H_{30}N_4O_4S_2$
Mol. Wt.: 430.17

To the bis-ethoxy lactim ether 5a (400 mg, 1.85 mmol) in dry EtOH (10 mL) was added a catalytic amount of $I_2$ (50 mg, 10% mmol) at rt. The mixture was stirred for 6~12 h under air until the analysis (TLC, silica gel) indicated the reaction was complete (new spot appeared under S.M. on the TLC plate). The organic solvent was evaporated under reduced pressure. The mixture which resulted was dissolved into EtOAc (20 mL), washed with sat. sodium thiosulfate (5~10 mL) and dried ($Na_2SO_4$). The solvent was then removed under reduced pressure which provided the dimer 5a-dimer: $^1$H NMR (300 MHz, $CDCl_3$) δ 1.32-1.36 (m, 6H), 3.27-3.30 (m, 3H), 4.08-4.22 (m, 6H), 4.39 (s, 1H); $^{13}$C NMR (75.5 MHz, $CDCl_3$): δ 14.7, 46.3, 47.5, 56.1, 61.5, 61.6, 162.7, 163.6; The NMR spectra was identical to its monomer except the S—H bond had disappeared. HRMS m/z (M+H)$^+$ calcd. 431.1787, found 431.1790.

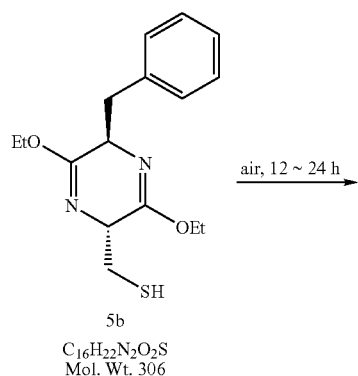

5b
$C_{16}H_{22}N_2O_2S$
Mol. Wt. 306

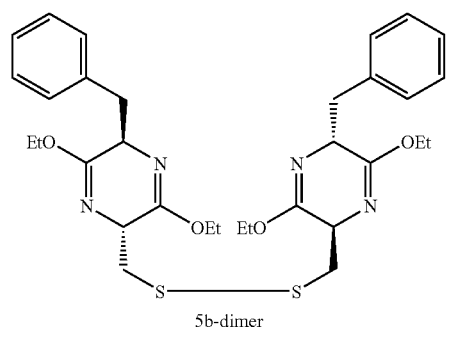

5b-dimer
$C_{32}H_{42}N_4O_4S_2$
Mol. Wt. 611

1,2-Bis(((2R,5R)-5-benzyl-3,6-diethoxy-2,5-dihydropyrazin-2-yl)methyl)disulfane (5b-dimer): was prepared in 65% yield following the procedure for preparation of 5a-dimer and obtained as a yellow liquid. 5b-dimer: $^1$H NMR (300 MHz, $CDCl_3$) δ 1.26-1.35 (m, 6H), 2.45-2.57 (m, 1H), 3.05-3.22 (m, 2H), 3.50-3.82 (m, 1H), 4.07-4.18 (m, 5H), 4.32-4.38 (m, 1H), 7.06-7.28 (m, 5H); $^{13}$C NMR (75.5 MHz, $CDCl_3$): δ 14.3, 39.6, 42.9, 43.0, 54.9, 57.1, 60.7, 60.8, 126.2, 126.5, 127.8, 137.0, 162.2, 162.6; The NMR spectra was identical to its monomer except the S—H bond had disappeared. HRMS m/z (M+H)$^+$ calcd. 611.2681, found 611.2677.

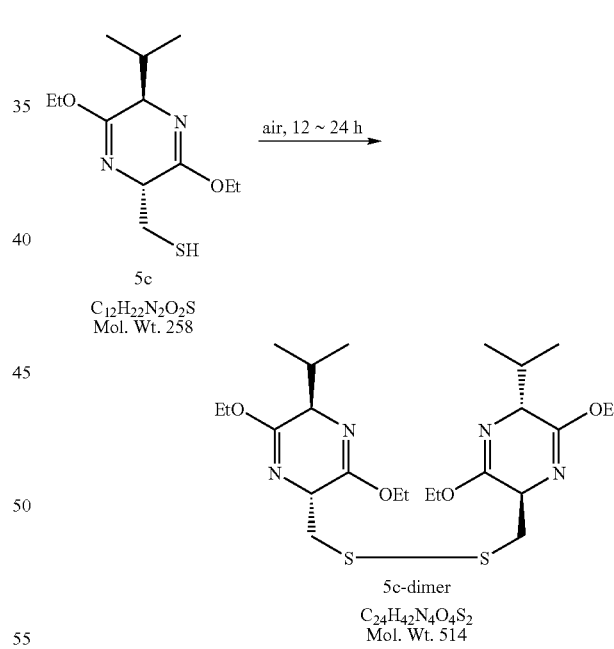

5c
$C_{12}H_{22}N_2O_2S$
Mol. Wt. 258

5c-dimer
$C_{24}H_{42}N_4O_4S_2$
Mol. Wt. 514

1,2-Bis(((2R,5R)-3,6-diethoxy-5-isopropyl-2,5-dihydropyrazin-2-yl)methyl)disulfane (5c-dimer): was prepared in 60% yield following the procedure for preparation of 5a-dimer and obtained as a colorless liquid. 5c-dimer: $^1$H NMR (300 MHz, $CDCl_3$) δ 0.76-0.78 (m, 3H), 1.06-1.09 (m, 3H), 1.25-1.31 (m, 6H), 2.18-2.23 (m, 1H), 2.82-3.01 (m, 1H), 3.21-3.45 (m, 1H), 3.54-3.70 (m, 2H), 4.07-4.33 (m, 4H); $^{13}$C NMR (75.5 MHz, $CDCl_3$): δ 14.2, 17.3, 31.1, 31.7, 45.2, 55.3, 60.5, 60.7, 161.0, 163.1; HRMS m/z (M+H)$^+$ calcd. 515.2726, found 515.2731.

Example 3

Alternative Route for Synthesis of Asymmetric Bis-Dipiperazinedione

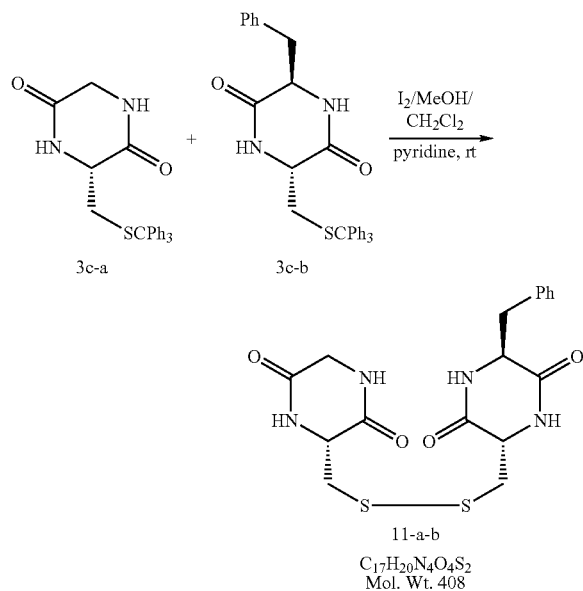

Bis[2,5-Piperazinedione, 3-(mercaptomethyl)-] (11-a-b): The trityl protected diketo-piperazine 3c-a (246 mg, 0.5 mmol) and 3c-b (201 mg, 0.5 mmol) were dissolved in a solution of methylene chloride (5 mL) and methanol (10 mL) with stirring. Pyridine (0.3 mL, 3.75 mmol) was then added to the resulting mixture, followed by a solution of iodine (126 mg, 0.5 mmol) in methanol (3 mL). The mixture was allowed to stir for 1 h at room temperature. No precipitate had formed by this time; however, TLC analysis indicated that the reaction was proceeding slowly by the appearance of a new spot under the starting material (UV light). A precipitate began to form within 2 h after concentrating the solution to a volume of 2 mL and methanol (5 mL) was added to result in a total volume of 10 mL. The solution was stirred an additional 23 h and the precipitate was filtered off. The solid was washed with cold methanol. The precipitate was filtered and dried to yield dimer 11-a-b as yellow solid (120 mg, 60%). 11-a-b: $^1$H NMR (300 MHz, DMSO-$d_6$) δ 2.89-2.91 (m, 2H), 3.09-3.21 (m, 3H), 3.33-3.87 (m, 4H), 4.11 (s, 1H), 4.21 (s, 1H), 7.13-7.36 (m, 5H), 8.07 (s, 1H), 8.32 (s, 2H), 8.58 (s, 1H); $^{13}$C NMR (75.5 MHz, DMSO-$d_6$) δ 42.3, 42.6, 43.1, 44.7, 53.3, 54.2, 54.3, 55.8, 127.2, 128.2, 130.6, 136.4, 165.9, 166.1, 166.5.

Example 4

Experimental for Scheme 4 and 5 Compounds

Representative Procedure for Synthesis of Protected Analogs (16)

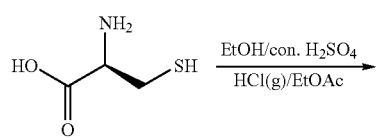

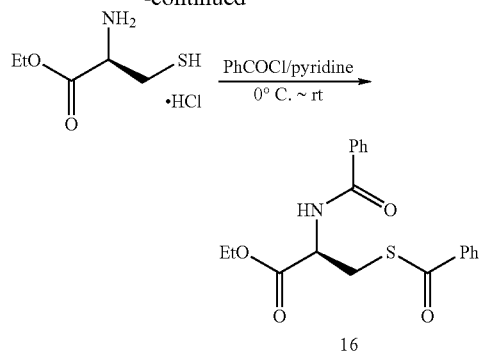

N,S-Dibenzoyl-L-cysteine Ethyl Ester (16): To a solution of pure L-cysteine ethyl ester hydrochloride (7.5 g, 40 mmol) in pyridine (30 mL) precooled at 0° C., benzyol chloride (10 mL) was added. After being kept for 1 h at room temperature, the mixture was poured onto ice. The precipitate was collected by filtration and was recrystallized from methanol in 88% yield (12 g). 16: m.p. 81° C.; $^1$H NMR (300 MHz, CDCl$_3$): δ 1.41 (t, J=6 Hz, 3H), 3.40-3.48 (m, 1H), 3.68-3.75 (m, 1H), 4.15 (q, J=7.11, 7.17 Hz, 2H), 4.62-4.70 (m, 1H), 7.48-7.57 (m, 5H), 7.66-7.69 (m, 1H), 7.84-7.93 (m, 4H), 9.02 (d, J=7.8 Hz, 1H); $^{13}$C NMR (75.5 MHz, CDCl$_3$): δ 14.4, 29.9, 52.6, 61.4, 127.2, 127.7, 128.7, 129.5, 132.0, 133.8, 134.5, 136.4, 166.8, 170.5, 191.0; HRMS m/z (M+H)$^+$ calcd. 358.1113, found 358.1106.

Representative Procedure for Synthesis of Compound 18 (Protected Analog 17 Coupling with Glycine)

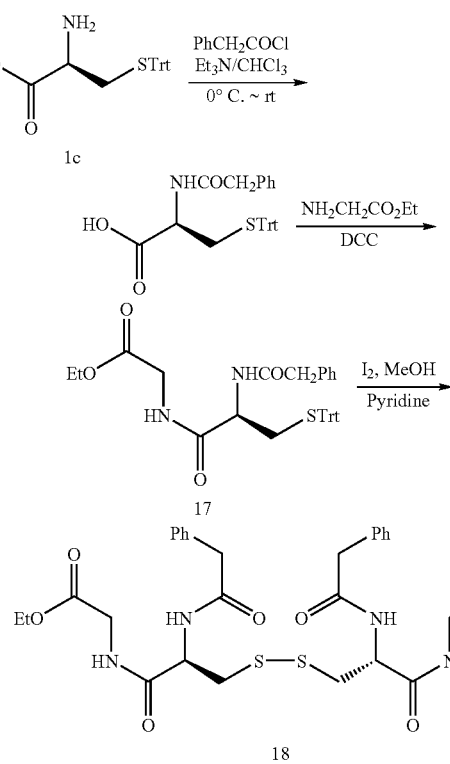

Preparation of Phenyl acetyl-S-trityl-L-cysteine: To a suspension of S-trityl-L-csyteine 1c (4.4 g, 12 mmol) in chloroform (92 mL) containing triethylamine (2.7 g, 26.4 mmol) cooled in ice, was added a solution of phenylacetyl chloride (1.8 g, 12 mmol) in chloroform (20 mL). The mixture was stirred at 0-5° C. for 15 min. and at room temperature for 24 hrs. Water was added (100 mL) and pH was adjusted to 1.5 with 5 N aqueous HCl. The aqueous phase was removed and the organic phase was washed with saturated sodium chloride (100 mL), dried ($Na_2SO_4$) and concentrated to give a white crystalline solid (4.9 g) in 85% yield. Phenyl acetyl-S-trityl-L-cysteine: m.p. 60-62° C.; $[\alpha]_D$=+21.8° (c 2, $CH_3OH$); $^1H$ NMR (300 MHz, $CDCl_3$): δ 2.60-2.71 (m, 2H), 3.5 (s, 1H), 4.15-4.23 (m, 1H), 5.92 (d, J=6.48 Hz, 1H), 7.21-7.33 (m, 20H); ); $^{13}C$ NMR (75.5 MHz, $CDCl_3$): δ 32.9, 43.1, 51.4, 67.8, 126.8, 127.2, 127.4, 127.8, 127.9, 128.4, 128.9, 129.1, 129.4, 144.1, 171.5, 172.5.

N-Carbobenzoxy-S-trityl-L-cysteinylglycine ethyl ester (17): To a solution of glycine ethyl ester hydrochloride (1.25 g, 9 mmol) in chloroform (50 mL) and triethylamine (1.25 mL) was added phenyl acetyl-S-trityl-L-cysteine (4.8 g, 10 mmol) and N,N'-dicyclohexycarbodiimide (2.1 g, 10 mmol). After stirred at room temperature overnight followed by addition of a few drops of 50% acetic acid the insoluble precipitate of dicyclohexylurea (1.7 g) was removed by filtration; the filtrate was washed successively with dilute hydrochloric acid, potassium hydrogen carbonate and water, dried over sodium sulfate and evaporated to dryness. The residue was treated with ethyl acetate. Some undissolved material (dicyclohexylurea, 0.5 g) was filtered off and the filtrate was concentrated in vacuo to a small volume. Crystalline 17 was separated out in 85% yield. 17: m.p. 152° C.; $^1H$ NMR (300 MHz, $CDCl_3$): δ 1.23-1.32 (m, 3H), 2.57-2.62 (m, 2H), 3.53 (s, 1H), 3.87-3.91 (m, 2H), 4.13 (d, J=6.18 Hz, 1H), 4.15-4.23 (m, 2H), 5.91 (d, J=7.41 Hz, 1H), 6.55 (s, 1H), 7.21-7.45 (m, 20H); $^{13}C$ NMR (75.5 MHz, $CDCl_3$): δ 14.0, 33.0, 41.3, 43.3, 51.9, 61.4, 67.0, 126.8, 127.3, 127.9, 128.9, 129.3, 129.5, 134.1, 144.3, 169.1, 169.9, 171.1.

Bis[(R)-ethyl 2-(3-mercapto-2-(2-phenylacetamido)propanamido)acetate] (18): was prepared in 72% yield following the procedure for preparation of 7a and obtained as a yellow solid. 18: m.p. 98° C.; $^1H$ NMR (300 MHz, $CDCl_3$); δ1.27-1.31 (m, 1H), 2.79-2.87 (m, 1H), 3.00-3.07 (m, 1H), 3.64 (s, 2H), 3.68-3.76 (m, 1H), 3.96-4.16 (m, 1H), 4.04-4.23 (m, 2H), 5.52-5.58 (m, 1H), 6.56 (d, J=9.15 Hz, 1H), 7.25-7.35 (m, 5H), 8.40-8.44 (s, 1H); $^{13}C$ NMR (75.5 MHz, $CDCl_3$): δ 14.1, 41.1, 43.1, 46.3, 53.0, 61.2, 127.2, 128.6, 129.5, 134.2, 169.1, 170.5, 171.5.

Example 5

Figure 4:
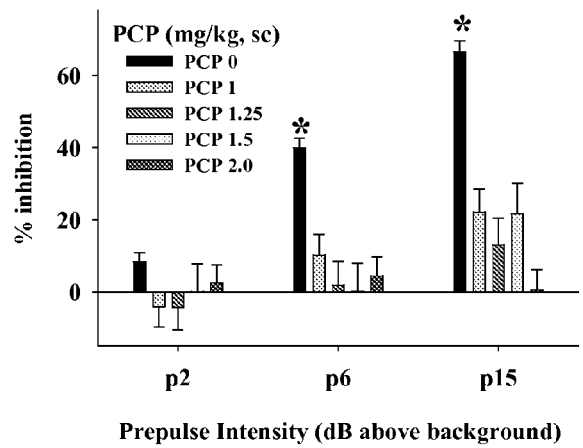
FIG. 4 illustrates percent inhibition of a startle response elicited by a loud auditory stimulus (50 dB above background) when preceded by a mild auditory stimulus (2-15 dB above background) in rats treated with pcp (0-2.0 mg/kg, N=9-60/group). * from every other group at respective prepulse intensity, Fisher LSD $p<0.05$ FIG. 5 displays the impact of N-acetyl cysteine on sensorimotor gating deficits produced by phencyclidine administered orally (left) or directly into the prefrontal cortex (right), which is likely the therapeutic site of action for cysteine prodrugs. * from every pcp only group at respective prepulse intensity, Fisher LSD $p<0.05$

PCP dose-dependently alters prepulse inhibition and impact of N-acetyl cysteine on sensorimotor gating deficits produced by PCP. Sensorimotor gating, a process compromised in schizophrenic patients, is often measured using prepulse inhibition whereby a mild auditory stimulus (prepulse, 2-15 db above background) precedes (100 ms) a startle-eliciting auditory stimulus (50 dB above background). Intact sensorimotor gating will result in suppression of the startle reflex when preceded by the prepulse. Since improvement in prepulse inhibition tracks improvement in symptoms that are largely insensitive to current treatments, this paradigm has become one of the most commonly used screening paradigms. FIG. 4 illustrates the capacity of PCP to disrupt prepulse inhibition, rendering the prepulse ineffective in suppressing the startle reflex. PCP is commonly used to disrupt prepulse inhibition because this abnormality, in addition to negative and cognitive symptoms, are insensitive to $1^{st}$ generation antipsychotics thereby providing predictive validity.

Figure 5:
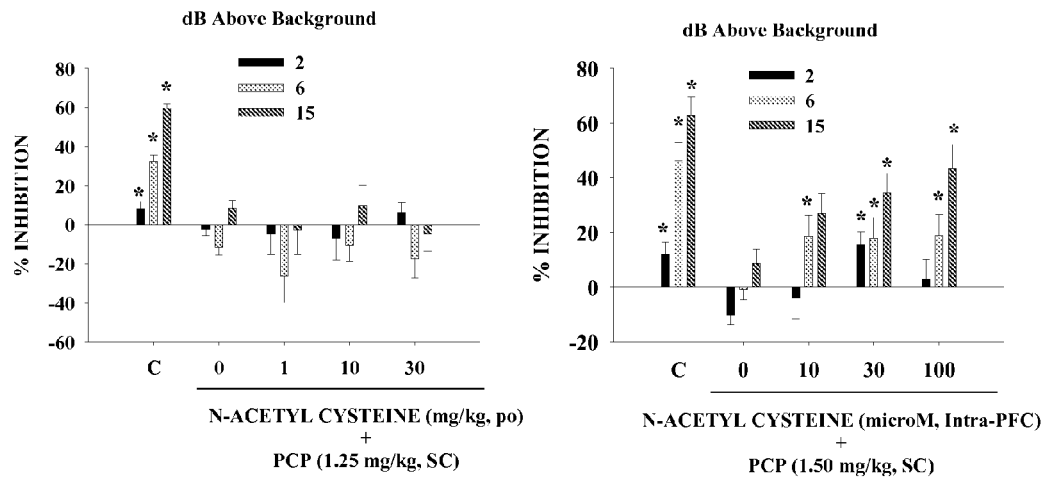

FIG. 5 illustrates the impact of N-acetyl cysteine on sensorimotor gating deficits produced by phencyclidine administered orally (left) or directly into the prefrontal cortex (right), which is likely the therapeutic site of action for cysteine prodrugs. N=6-46/group. * indicate a significant difference from rats receiving PCP only (e.g., 0 N-acetyl cysteine), Fisher LSD, p, 0.05.

Example 6

Figure 6:
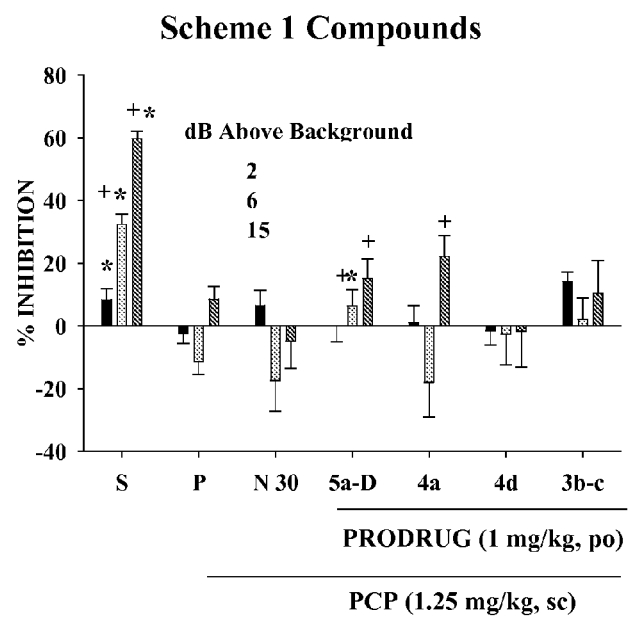
FIG. 6 illustrates the efficacy of exemplary compounds from Scheme 1 relative to N-acetyl cysteine in reversing PCP-induced deficits in sensorimotor gating in rats. * from every pcp only group at respective prepulse intensity, +NAC 30 group, Fisher LSD $p<0.05$

Efficacy of compounds from scheme 1 relative to N-acetyl cysteine in reversing PCP-induced deficits in sensorimotor gating in rats. FIG. 6 is a bar graph illustrating inhibition of a startle response in response to a load stimulus (pulse) when preceded by a pre-pulse stimulus (2-15 db above background). Prepulse inhibition is a commonly used paradigm to screen antipsychotic agents for use in treating schizophrenia. The pre-pulse stimulus presented at 15 dB above background reduced the startle response in saline controls (S; N=46) by >60% relative to the response elicited following exposure to the pulse only. Rats pretreated with phencyclidine only (P; 1.25 mg/kg, SC; N=42) failed to exhibit a reduction in the response elicited by the pulse even when preceded by the pre-pulse (regardless of stimulus intensity). This reflects sensorimotor gating deficits common to patients afflicted with schizophrenia. Rats pretreated (60 min) with N-acetyl cysteine (30 mg/kg, po) failed to exhibit sensorimotor gating. Note direct delivery of N-acetyl cysteine into the brain reverses phencyclidine-induced deficits in sensorimotor gating, which is consistent with clinical trials establishing the antipsychotic efficacy of this compound. Rats pretreated (60 min) with compounds synthesized from scheme 1 (N=7-22/group), notably compounds 5a-D and 4a, exhibited a significant difference relative to either rats receiving PCP alone (*, Fisher LSD, p<0.05) and/or N-acetylcysteine (N 30; 30 mg/kg; +, Fisher LSD, p<0.05). Collectively, these data indicate the efficacy of these compounds and this synthesis scheme to generate novel antipsychotics that exceeds the potential of N-acetyl cysteine.

Example 7

Figure 7:
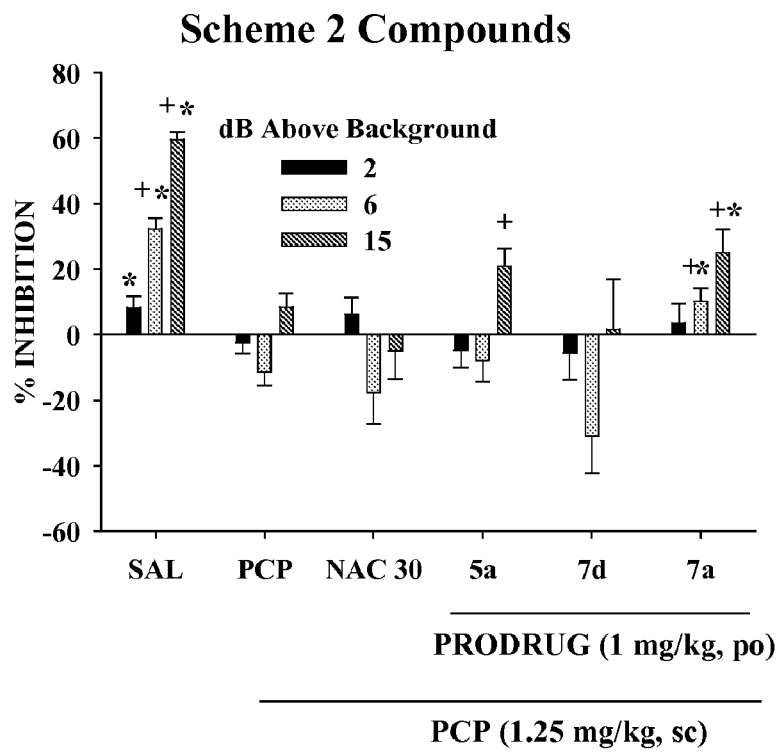
FIG. 7 shows the efficacy of exemplary compounds from Scheme 2 relative to N-acetyl cysteine in reversing PCP-induced deficits in sensorimotor gating in rats. * from every pcp only group at respective prepulse intensity, +NAC 30 group, Fisher LSD $p<0.05$

Efficacy of compounds from scheme 2 relative to N-acetyl cysteine in reversing PCP-induced deficits in sensorimotor gating in rats. FIG. 7 is a bar graph illustrating inhibition of a startle response in response to a load stimulus (pulse) when preceded by a pre-pulse stimulus (2-15 db above background). Prepulse inhibition is a commonly used paradigm to screen antipsychotic agents for use in treating schizophrenia. The pre-pulse stimulus presented at 15 dB above background reduced the startle response in saline controls (S; N=46) by >60% relative to the response elicited following exposure to the pulse only. Rats pretreated with phencyclidine only (P; 1.25 mg/kg, SC; N=42) failed to exhibit a reduction in the response elicited by the pulse even when preceded by the pre-pulse (regardless of stimulus intensity). This reflects sensorimotor gating deficits common to patients afflicted with schizophrenia. Rats pretreated (60 min) with N-acetyl cysteine (30 mg/kg, po) failed to exhibit sensorimotor gating. Note direct delivery of N-acetyl cysteine into the brain reverses phencyclidine-induced deficits in sensorimotor gating, which is consistent with clinical trials establishing the antipsychotic efficacy of this compound. Rats pretreated (60 min) with compounds synthesized from scheme 2 (N=7-14/group), notably compounds 5a and 7a, exhibited a significant difference relative to either rats receiving PCP alone (*, Fisher LSD, p<0.05) and/or N-acetylcysteine (N 30; 30 mg/kg; +, Fisher LSD, p<0.05). Collectively, these data indicate the efficacy of these compounds and this synthesis scheme to generate novel antipsychotics that exceeds the potential of N-acetyl cysteine.

Example 8

Figure 8:
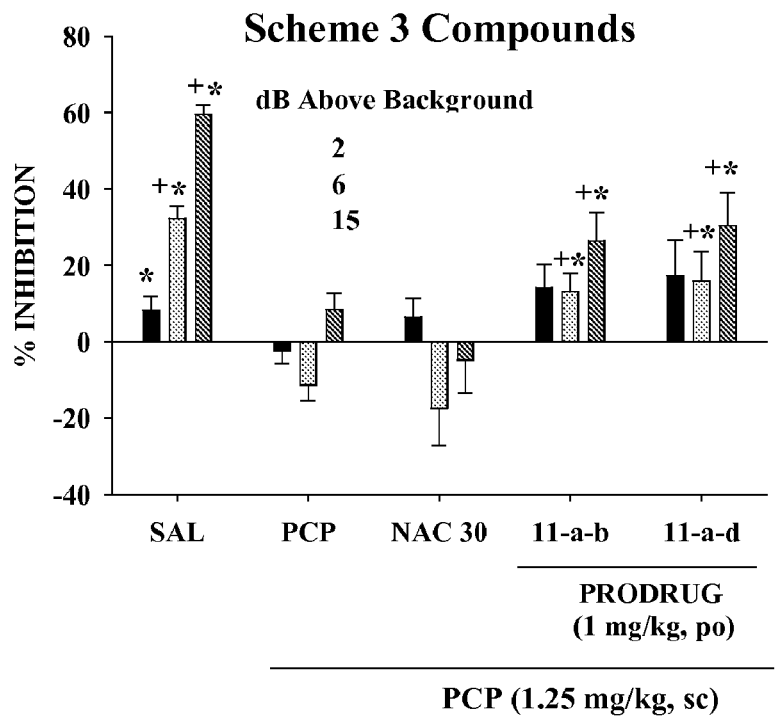
FIG. 8 illustrates the efficacy of exemplary compounds from Scheme 3 relative to N-acetyl cysteine in reversing PCP-induced deficits in sensorimotor gating in rats. * from every pcp only group at respective prepulse intensity, +NAC 30 group, Fisher LSD $p<0.05$

Efficacy of compounds from scheme 3 relative to N-acetyl cysteine in reversing PCP-induced deficits in sensorimotor gating in rats. FIG. 8 is a bar graph illustrating inhibition of a startle response in response to a load stimulus (pulse) when preceded by a pre-pulse stimulus (2-15 db above background). Prepulse inhibition is a commonly used paradigm to screen antipsychotic agents for use in treating schizophrenia. The pre-pulse stimulus presented at 15 dB above background reduced the startle response in saline controls (S; N=46) by >60% relative to the response elicited following exposure to the pulse only. Rats pretreated with phencyclidine only (P; 1.25 mg/kg, SC; N=42) failed to exhibit a reduction in the response elicited by the pulse even when preceded by the pre-pulse (regardless of stimulus intensity). This reflects sensorimotor gating deficits common to patients afflicted with schizophrenia. Rats pretreated (60 min) with N-acetyl cysteine (30 mg/kg, po) failed to exhibit sensorimotor gating. Note direct delivery of N-acetyl cysteine into the brain reverses phencyclidine-induced deficits in sensorimotor gating, which is consistent with clinical trials establishing the antipsychotic efficacy of this compound. Rats pretreated (60 min) with compounds synthesized from scheme 3 (N=7/group), namely compounds 11-a-b and 11-a-d, exhibited a significant difference relative to either rats receiving PCP alone (*, Fisher LSD, p<0.05) and/or N-acetylcysteine (N 30; 30 mg/kg; +, Fisher LSD, p<0.05). Collectively, these data indicate the efficacy of these compounds and this synthesis scheme to generate novel antipsychotics that exceeds the potential of N-acetyl cysteine.

Example 9

Figure 9:
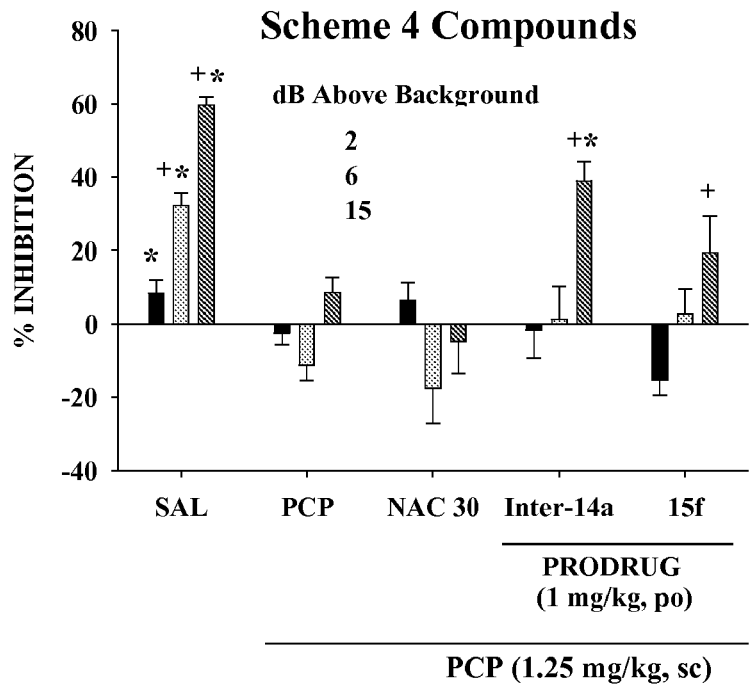
FIG. 9 shows the efficacy of exemplary compounds from Scheme 4 relative to N-acetyl cysteine in reversing PCP-induced deficits in sensorimotor gating in rats. * from every pcp only group at respective prepulse intensity, +NAC 30 group, Fisher LSD $p<0.05$

Efficacy of compounds from scheme 4 relative to N-acetyl cysteine in reversing PCP-induced deficits in sensorimotor gating in rats. FIG. 9 is a bar graph illustrating inhibition of a startle response in response to a load stimulus (pulse) when preceded by a pre-pulse stimulus (2-15 db above background). Prepulse inhibition is a commonly used paradigm to screen antipsychotic agents for use in treating schizophrenia. The pre-pulse stimulus presented at 15 dB above background reduced the startle response in saline controls (S; N=46) by >60% relative to the response elicited following exposure to the pulse only. Rats pretreated with phencyclidine only (P; 1.25 mg/kg, SC; N=42) failed to exhibit a reduction in the response elicited by the pulse even when preceded by the pre-pulse (regardless of stimulus intensity). This reflects sensorimotor gating deficits common to patients afflicted with schizophrenia. Rats pretreated (60 min) with N-acetyl cysteine (30 mg/kg, po) failed to exhibit sensorimotor gating. Note direct delivery of N-acetyl cysteine into the brain reverses phencyclidine-induced deficits in sensorimotor gating, which is consistent with clinical trials establishing the antipsychotic efficacy of this compound. Rats pretreated (60 min) with compounds synthesized from scheme 4 (N=7/group), namely the intermediate to compound 14a (Inter-14a) and compound 15f, exhibited a significant difference relative to either rats receiving PCP alone (*, Fisher LSD, p<0.05) and/or N-acetylcysteine (N 30; 30 mg/kg; +, Fisher LSD, p<0.05). Collectively, these data indicate the efficacy of these compounds and this synthesis scheme to generate novel antipsychotics that exceeds the potential of N-acetyl cysteine.

Example 10

Figure 10:
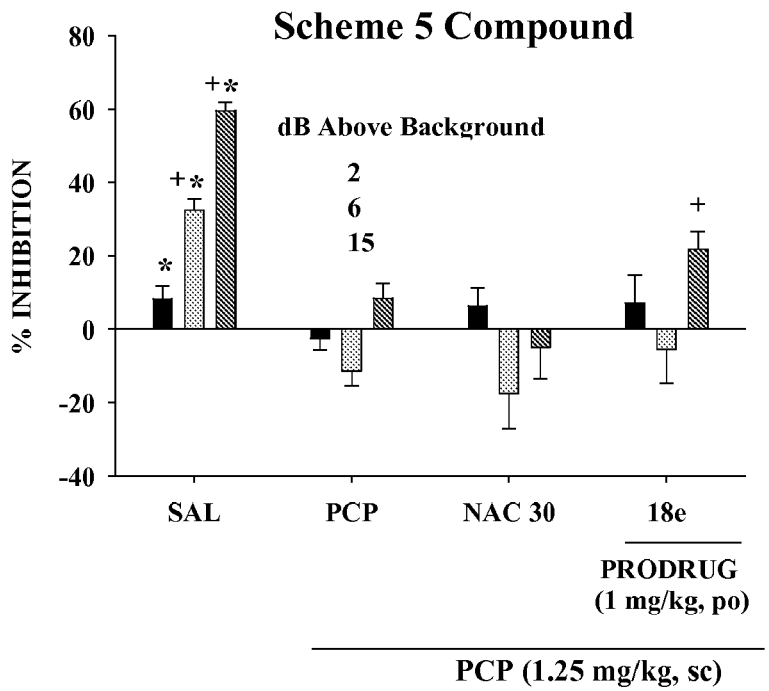
FIG. 10 illustrates the efficacy of compound from scheme 5 relative to N-acetyl cysteine in reversing PCP-induced deficits in sensorimotor gating in rats. * from every pcp only group at respective prepulse intensity, +NAC 30 group, Fisher LSD $p<0.05$ FIG. 11 provides a bar graph illustrating that N-acetylcysteine (IP) is effective in producing a significant reduction in cocaine-induced reinstatement at the doses of 30 and 60 mg/kg.

Efficacy of compound from scheme 5 relative to N-acetyl cysteine in reversing PCP-induced deficits in sensorimotor gating in rats. FIG. 10 is a bar graph illustrating inhibition of a startle response in response to a load stimulus (pulse) when preceded by a pre-pulse stimulus (2-15 db above background). Prepulse inhibition is a commonly used paradigm to screen antipsychotic agents for use in treating schizophrenia. The pre-pulse stimulus presented at 15 dB above background reduced the startle response in saline controls (S; N=46) by >60% relative to the response elicited following exposure to the pulse only. Rats pretreated with phencyclidine only (P; 1.25 mg/kg, SC; N=42) failed to exhibit a reduction in the response elicited by the pulse even when preceded by the pre-pulse (regardless of stimulus intensity). This reflects sensorimotor gating deficits common to patients afflicted with schizophrenia. Rats pretreated (60 min) with N-acetyl cysteine (30 mg/kg, po) failed to exhibit sensorimotor gating. Note direct delivery of N-acetyl cysteine into the brain reverses phencyclidine-induced deficits in sensorimotor gating, which is consistent with clinical trials establishing the antipsychotic efficacy of this compound. Rats pretreated (60 min) with a compound (18e) synthesized from scheme 5 (N=7) exhibited a significant difference relative to either rats receiving N-acetylcysteine (N 30; 30 mg/kg; +, Fisher LSD, p<0.05). Collectively, these data indicate the efficacy of this compound and synthesis scheme to generate novel antipsychotics that exceeds the potential of N-acetyl cysteine.

Example 11

Figure 11:
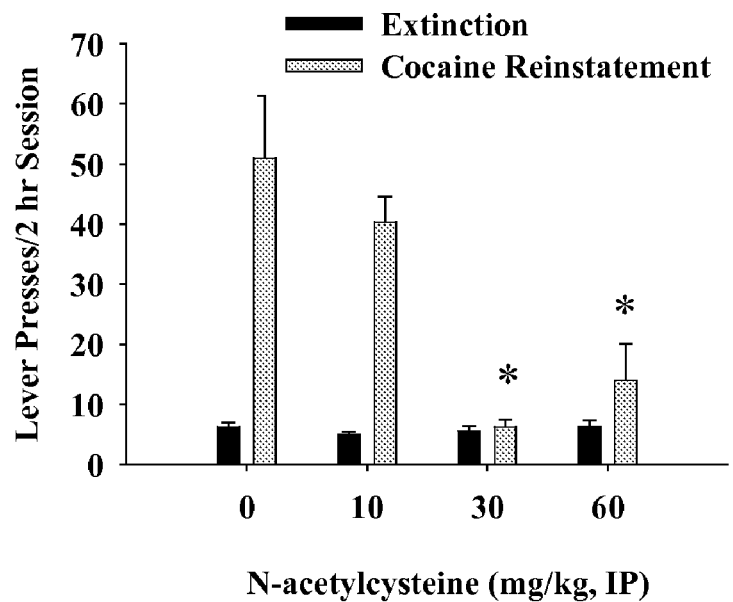
Figure 12:
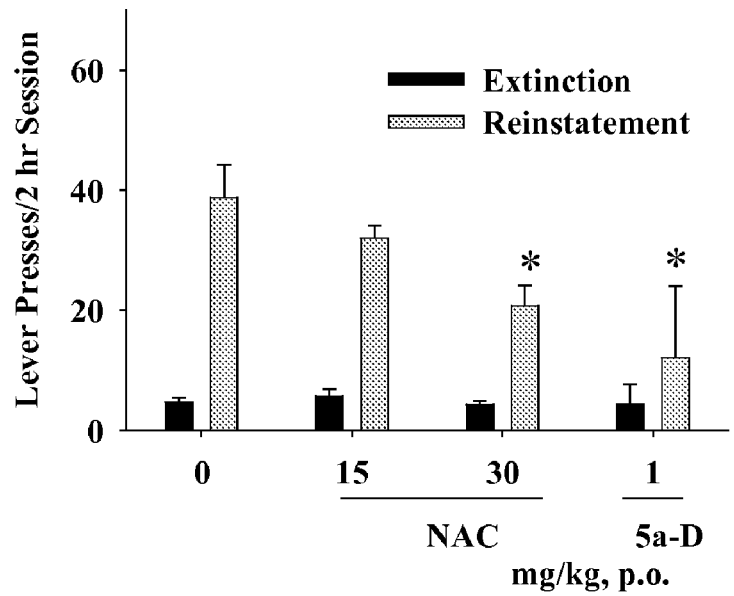
FIG. 12 depicts a bar graph illustrating that N-acetylcysteine is less effective when given orally. Further, administration of 1 mg/kg of Compound 5a-D (Scheme 1) was sufficient to block cocaine-induced reinstatement, an effect that was comparable to 30 mg/kg NAC.

Efficacy of compound 5a-d (Scheme 1) as novel anticraving agent. In addition to normalizing the function of the prefrontal cortex, as demonstrated by the impact of the prodrugs on pcp-induced sensorimotor gating deficits, the anticraving potential of a drug can be demonstrated using the extinction/reinstatement paradigm. In the present experiments, rats were implanted with indwelling jugular catheters with an external port affixed slightly posterior to the rat's shoulder blades. Tubing is used to connect a syringe of cocaine to the external port of the indwelling catheter. Rats are then placed into standard operant chambers (Med Associates) and permitted to press a lever for an infusion of cocaine (0.5 mg/kg/200 microL, IV). Once behavior is stable, rats are permitted at least eleven 2-hr sessions to self-administer cocaine. Afterwards, the cocaine solution is replaced with saline in order to extinguish lever pressing. Once responding decreases to 10 or fewer lever presses/2 hr sessions for 3 out of 4 daily sessions, rats are tested for reinstatement (relapse). To do this, rats are placed into the operant chamber and vehicle or a cysteine/cystine prodrug (1-60 mg/kg, p.o.; N=2-17) is administered. Afterwards, rats then receive an injection of cocaine (10 mg/kg, IP). Responding is then assessed for 120 min. Data depicted in FIG. 11 illustrate that N-acetyl cysteine (IP) is effective in producing a significant reduction in cocaine-induced reinstatement at the doses of 30 and 60 mg/kg (IP; * indicates a significant decrease in responding relative to rats treated with 0 NAC, Fisher LSD). FIG. 12 demonstrates that N-acetylcysteine is less effective when given orally. Further, administration of 1 mg/kg of Compound 5a-d (Scheme 1) was sufficient to block cocaine-induced reinstatement, an effect that was comparable to 30 mg/kg NAC (* indicates a significant decrease in responding relative to rats treated with 0 NAC, Fisher LSD).

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. All publications, patents and patent applications cited herein are hereby incorporated by reference in their entirety for all purposes.

What is claimed is:

1. A method of treating schizophrenia in a subject comprising administering to said subject an effective amount of a cysteine prodrug having the structure:

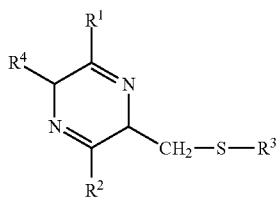

wherein: $R^1$ and $R^2$ are independently selected from OH, =O, or a branched or straight chain $C_1$ to $C_5$ alkoxy group, with the caveat that when =O is selected the nitrogen atom adjacent the carbonyl group thusly formed bears a H and a single bond joins the adjacent nitrogen to said carbonyl group;

$R^3$ is H, a branched or straight chain $C_1$ to $C_5$ alkyl, a nitrobenzenesulfonyl, a trityl, an aryl thio, an aryl, an alkylthio, an acyl, a benzoyl, a thio acyl, a thio benzoyl, or a benzyl group; and $R^4$ is selected from the side chain groups of the natural L-amino acids cys, gly, phe, pro, val, ser, arg, asp, asn, glu, gln, ala, his, ile, leu, lys, met, thr, trp, tyr, or D-stereoisomers thereof, wherein when $R^4$ is the pro side chain group, $R^4$ consists of —$CH_2CH_2CH_2$— that bridges the carbon atom to which $R^4$ is attached to the adjoining nitrogen atom; or, a cystine dimer of said prodrug having the structure:

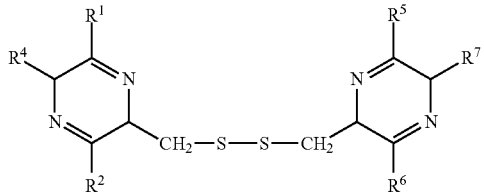

wherein: $R^1$, $R^{2,}$ $R^5$ and $R^6$ are independently selected from OH, =O, or a branched or straight chain $C_1$ to $C_5$ alkoxy group, with the caveat that when =O is selected the nitrogen atom adjacent the carbonyl group thusly formed bears a H and a single bond joins the adjacent nitrogen to said carbonyl group; and $R^4$ and $R^7$ are independently selected from the side chain groups of the natural L-amino acids cys, gly, phe, pro, val, ser, arg, asp, asn, glu, gln, ala, his, ile, leu, lys, met, thr, trp, tyr, or D-stereoisomers thereof, wherein when $R^4$ is the pro side chain group, $R^4$ consists of —$CH_2CH_2CH_2$— that bridges the carbon atom to which $R^4$ is attached to the adjoining nitrogen atom, and when $R^7$ is the pro side chain group, $R^7$ consists of —$CH_2CH_2CH_2$— that bridges the carbon atom to which $R^7$ is attached to the adjoining nitrogen atom, whereby schizophrenia is treated in said subject.

2. The method according to claim 1, wherein said cysteine prodrug in the form of the cystine dimer is administered, and wherein the $R^4$ and $R^7$ groups of the cystine dimer are identical.

3. The method according to claim 1, wherein said cysteine prodrug in the form of the cystine dimer is administered, and wherein the $R^4$ and $R^7$ groups of the cystine dimer are not identical.

4. The method according to claim 1, wherein at least one of $R^4$ and $R^7$ of said cysteine prodrug or cystine dimer thereof is —$CH_2SH$, and wherein said —$CH_2SH$ is further protected by a branched or straight chain $C_1$ to $C_5$ alkyl, a nitrobenzenesulfonyl, a trityl, an aryl thio, an aryl, an alkylthio, an acyl, a benzoyl, a thio acyl, a thio benzoyl, or a benzyl group.

5. The method according to claim 1, wherein said cysteine prodrug has the structure:

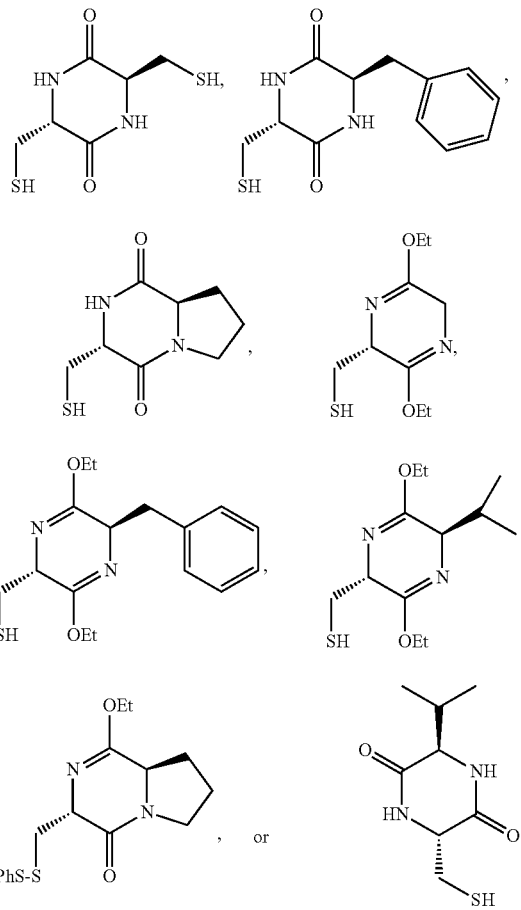

6. The method according to claim 1, wherein said cysteine prodrug is in the form of the cystine dimer having the structure:
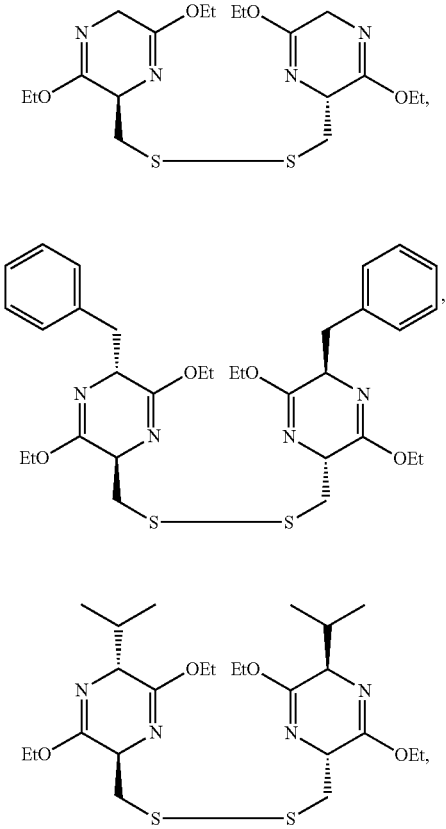
-continued
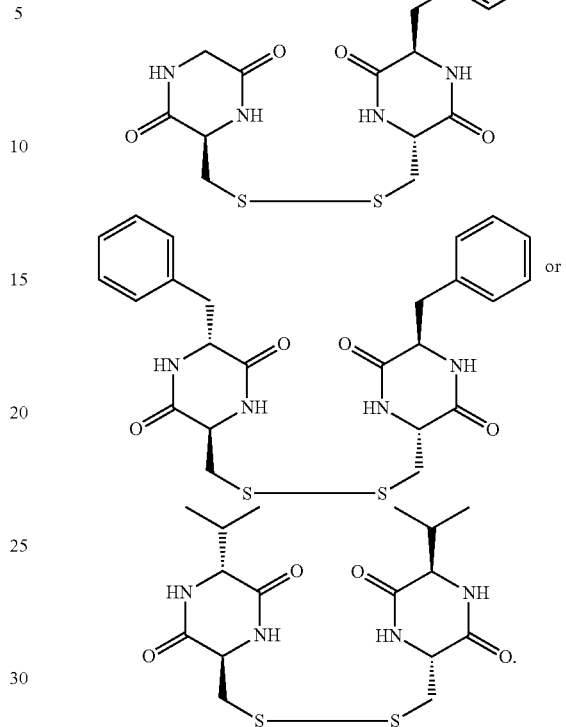
7. The method according to claim 1, wherein the step of administering to said subject is accomplished by oral delivery.
* * * * *